(12) United States Patent  
Phillips

(10) Patent No.: US 7,879,110 B2  
(45) Date of Patent: Feb. 1, 2011

(54) FOOT PROSTHESIS HAVING CUSHIONED ANKLE

(75) Inventor: Van L. Phillips, Albion, CA (US)

(73) Assignee: Ossur hf (IS)

( * ) Notice: Subject to any disclaimer, the term of this patent is extended or adjusted under 35 U.S.C. 154(b) by 0 days.

(21) Appl. No.: 12/628,996

(22) Filed: Dec. 1, 2009

(65) Prior Publication Data

US 2010/0106260 A1    Apr. 29, 2010

Related U.S. Application Data

(60) Continuation of application No. 11/868,457, filed on Oct. 5, 2007, now Pat. No. 7,648,533, which is a division of application No. 10/776,123, filed on Feb. 11, 2004, now Pat. No. 7,279,011, which is a division of application No. 09/698,489, filed on Oct. 26, 2000, now Pat. No. 6,899,737.

(51) Int. Cl.  
*A61F 2/66* (2006.01)

(52) U.S. Cl. ........................................ 623/52

(58) Field of Classification Search .............. 623/47–57  
See application file for complete search history.

(56) References Cited

U.S. PATENT DOCUMENTS

| | | |
|---|---|---|
| 25,238 A | 8/1859 | Bly |
| 53,931 A | 4/1866 | Weston |
| 56,983 A | 8/1866 | Nicholas |
| 57,666 A | 9/1866 | Bly |
| 368,580 A | 8/1887 | Frees |

(Continued)

FOREIGN PATENT DOCUMENTS

BE          1701482          6/1955

(Continued)

OTHER PUBLICATIONS

English Translation of previously submitted Japanese Office Action dated Nov. 13, 2007 from Application No. 551880/1999.

(Continued)

*Primary Examiner*—Suzette J Gherbi  
(74) *Attorney, Agent, or Firm*—Knobbe, Martens, Olson & Bear LLP

(57) ABSTRACT

A simple, inexpensive prosthetic foot is provided incorporating a cushioned ankle including an ankle block formed of a resilient material or bladder having desired compliance and energy return characteristics. The ankle block is sandwiched between a foot element and an ankle element. One or more openings extends through the ankle block with a substantially transverse orientation relative to a forward walking motion. The size and shape of these openings, as well as the insertion of different types of stiffeners therein, provide desired performance characteristics to the ankle block. When the ankle block takes the form of one or more inflatable bladders, the pressure within these bladders is individually controlled by valves to provide desired performance characteristics to different portions of the prosthetic foot. A pump system can also be used to control and generate fluid pressure into these bladders. A preferred pump system generates fluid pressure based upon the movement of the amputee onto two telescoping pylons that are connected to the prosthetic foot.

20 Claims, 26 Drawing Sheets

U.S. PATENT DOCUMENTS

| | | | |
|---|---|---|---|
| 487,697 A | 12/1892 | Ehle |
| 508,034 A | 11/1893 | Moore |
| 534,198 A | 2/1895 | Chapman |
| 561,979 A | 6/1896 | Erickson |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 1,056,426 A | 3/1913 | Kenny |
| 1,069,001 A | 7/1913 | Guy |
| 1,704,065 A | 3/1926 | Smith |
| 1,649,773 A | 11/1927 | Witmyer |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,556,525 A | 6/1951 | Drennon |
| 2,570,735 A | 10/1951 | Weise |
| 2,594,945 A | 4/1952 | Lucas et al. |
| 2,692,392 A | 10/1954 | Bennington et al. |
| 2,731,645 A | 1/1956 | Woodall |
| 2,996,295 A | 8/1961 | Smith |
| 3,098,239 A | 7/1963 | Nader |
| 3,551,914 A | 1/1971 | Woodall |
| 3,671,980 A | 6/1972 | Baird |
| 3,754,286 A | 8/1973 | Ryan |
| 3,766,569 A | 10/1973 | Orange |
| 3,784,988 A | 1/1974 | Trumpler |
| 3,833,941 A | 9/1974 | Wagner |
| 3,874,004 A | 4/1975 | May |
| 3,982,280 A | 9/1976 | Asbelle et al. |
| 3,995,324 A | 12/1976 | Burch |
| 4,007,497 A | 2/1977 | Haupt |
| 4,051,558 A | 10/1977 | Vallotton |
| 4,091,472 A | 5/1978 | Daher et al. |
| 4,177,525 A | 12/1979 | Arbogast et al. |
| 4,225,982 A | 10/1980 | Cochrane et al. |
| 4,229,839 A | 10/1980 | Schwemmer |
| 4,328,594 A | 5/1982 | Campbell et al. |
| 4,360,931 A | 11/1982 | Hampton |
| 4,387,472 A | 6/1983 | Wilson |
| 4,463,459 A | 8/1984 | Shorter et al. |
| 4,547,913 A | 10/1985 | Phillips |
| 4,555,817 A | 12/1985 | McKendrick |
| 4,645,509 A | 2/1987 | Poggi et al. |
| 4,652,266 A | 3/1987 | Truesdell |
| 4,718,913 A | 1/1988 | Voisin |
| 4,721,510 A | 1/1988 | Cooper et al. |
| 4,892,553 A | 1/1990 | Prahl |
| 4,892,554 A | 1/1990 | Robinson |
| 4,959,073 A | 9/1990 | Merlette |
| 5,007,938 A | 4/1991 | Prahl |
| 5,019,109 A | 5/1991 | Voisin |
| 5,030,239 A | 7/1991 | Copes |
| 5,062,859 A | 11/1991 | Naeder |
| 5,066,305 A | 11/1991 | Firth |
| 5,085,665 A | 2/1992 | Radocy et al. |
| 5,108,456 A | 4/1992 | Coonan, III |
| 5,112,356 A | 5/1992 | Harris et al. |
| 5,116,383 A | 5/1992 | Shorter et al. |
| 5,116,384 A | 5/1992 | Wilson et al. |
| 5,116,385 A | 5/1992 | Allard et al. |
| 5,156,631 A | 10/1992 | Merlette |
| 5,156,632 A | 10/1992 | Wellershaus |
| 5,181,932 A | 1/1993 | Phillips |
| 5,185,570 A | 2/1993 | Fitzpatrick |
| 5,219,365 A | 6/1993 | Sabolich |
| 5,258,038 A | 11/1993 | Robinson et al. |
| 5,258,039 A | 11/1993 | Goh et al. |
| 5,290,319 A | 3/1994 | Phillips |
| 5,376,133 A | 12/1994 | Gramnas |
| 5,376,140 A | 12/1994 | Ryan |
| 5,376,141 A * | 12/1994 | Phillips .................... 623/55 |
| 5,387,246 A | 2/1995 | Phillips |
| 5,405,409 A | 4/1995 | Knoth |
| 5,405,411 A | 4/1995 | McCoy |
| 5,443,527 A | 8/1995 | Wilson |
| 5,443,529 A | 8/1995 | Phillips |
| 5,495,682 A | 3/1996 | Chen |
| 5,507,836 A | 4/1996 | Pohlig |
| 5,509,938 A | 4/1996 | Phillips |
| 5,701,686 A | 12/1997 | Berr et al. |
| 5,728,177 A | 3/1998 | Phillips |
| 5,800,569 A | 9/1998 | Phillips |
| 5,888,239 A | 3/1999 | Wellershaus et al. |
| 5,899,944 A | 5/1999 | Phillips |
| 5,904,721 A | 5/1999 | Henry et al. |
| 5,913,902 A | 6/1999 | Geible |
| 5,941,913 A | 8/1999 | Woolnough et al. |
| 5,984,972 A | 11/1999 | Huston et al. |
| 5,993,488 A | 11/1999 | Phillips |
| 6,007,582 A | 12/1999 | May |
| 6,129,766 A | 10/2000 | Johnson et al. |
| 6,182,378 B1 | 2/2001 | Sendaula |
| 6,206,934 B1 * | 3/2001 | Phillips .................... 623/53 |
| 6,261,324 B1 | 7/2001 | Merlette |
| 6,280,479 B1 * | 8/2001 | Phillips .................... 623/52 |
| 6,281,594 B1 | 8/2001 | Sarich |
| 6,350,286 B1 | 2/2002 | Atkinson et al. |
| 6,398,818 B1 | 6/2002 | Merlette et al. |
| 7,063,727 B2 * | 6/2006 | Phillips et al. ............ 623/52 |
| 7,279,011 B2 * | 10/2007 | Phillips .................... 623/53 |
| 2002/0040249 A1 | 4/2002 | Phillips |
| 2002/0077706 A1 | 6/2002 | Phillips |
| 2002/0133237 A1 | 9/2002 | Christesen |
| 2002/0183860 A1 | 12/2002 | Wilkinson et al. |
| 2003/0093158 A1 | 5/2003 | Phillips |
| 2003/0120353 A1 | 6/2003 | Christensen |
| 2004/0068327 A1 | 4/2004 | Christensen |
| 2004/0162623 A1 | 8/2004 | Phillips |

FOREIGN PATENT DOCUMENTS

| | | |
|---|---|---|
| BE | 888671 | 8/1981 |
| DE | 94444 | 2/1897 |
| DE | 308671 | 10/1918 |
| DE | 322909 | 6/1919 |
| DE | 393281 | 10/1922 |
| DE | 363938 | 11/1922 |
| DE | 366553 | 1/1923 |
| DE | 392080 | 1/1923 |
| DE | 379849 | 8/1923 |
| DE | 502698 | 7/1930 |
| DE | 811714 | 6/1951 |
| DE | 168634 | 7/1951 |
| DE | 813191 | 7/1951 |
| DE | 817186 | 8/1951 |
| DE | 832473 | 1/1952 |
| DE | 834884 | 2/1952 |
| DE | 838480 | 2/1952 |
| DE | 924230 | 2/1955 |
| DE | 1174328 | 4/1957 |
| DE | 1891505 | 4/1964 |
| DE | 1897509 | 7/1964 |
| DE | 1491182 | 11/1965 |
| DE | 1941762 | 7/1966 |
| DE | 1954486 | 2/1967 |
| DE | 3239959 | 10/1982 |
| DE | 8417477 | 7/1984 |
| DE | 1754533 | 10/1987 |
| EP | 0 401 864 | 6/1990 |
| EP | 40184 | 6/1990 |
| FR | 661071 | 7/1929 |
| FR | 1005124 | 4/1952 |

| | | |
|---|---|---|
| FR | 1213026 | 3/1960 |
| FR | 1251230 | 12/1960 |
| FR | 2410998 | 7/1979 |
| FR | 2640499 | 6/1990 |
| FR | 2673370 | 4/1992 |
| GB | 10082 | 7/1915 |
| GB | 117547 | 10/1917 |
| GB | 120462 | 11/1918 |
| GB | 139936 | 3/1920 |
| GB | 275902 | 9/1927 |
| GB | 621576 | 4/1949 |
| GB | 625528 | 6/1949 |
| GB | 1371996 | 10/1974 |
| GB | 2008410 | 11/1978 |
| JP | 09084814 | 3/1997 |
| JP | 09084814 A2 | 3/1997 |
| RU | 778-732 | 8/1997 |
| SU | 137843 | 9/1961 |
| SU | 311635 | 4/1970 |
| SU | 322198 | 2/1972 |
| SU | 806023 | 4/1977 |
| SU | 560606 | 6/1977 |
| SU | 778732 | 8/1977 |
| SU | 679208 | 8/1979 |
| SU | 1454-449 A1 | 11/1986 |
| SU | 1391-643 A | 4/1988 |
| SU | 1600759 | 9/1988 |
| SU | 1519588 | 11/1989 |
| WO | WO 88/00815 | 2/1988 |
| WO | WO 88/06431 | 9/1988 |
| WO | WO 94/18914 | 9/1994 |
| WO | WO 96/04869 | 2/1996 |
| WO | WO 98/53769 | 3/1998 |
| WO | WO 99/05991 | 2/1999 |
| WO | WO 99/52476 | 10/1999 |
| WO | WO 00/27317 | 5/2000 |

OTHER PUBLICATIONS

Japanese Office Action (English translation), dated Feb. 6, 2007, from application No. 551880/1999.
Japanese Office Action, dated Nov. 13, 2007, from application No. 551880/1999.
PCT Search Report dated Jan. 22, 2003, from International Application No. PCT/US01/50834.
The Springlite Foot, The Design Process for a Novel Advanced Composite Prosthesis, Merlett, John and John Tsamisis, from Composites in Manufacturing Case Studies, pp. 269-288, Copyright 1991.
The College Park Venture Foot, College Park Industries (CPI), www.college-park.com, published 2004.
The College Park Tribute, College Park Industries (CPI), www.college-park.com, published 2004.

* cited by examiner

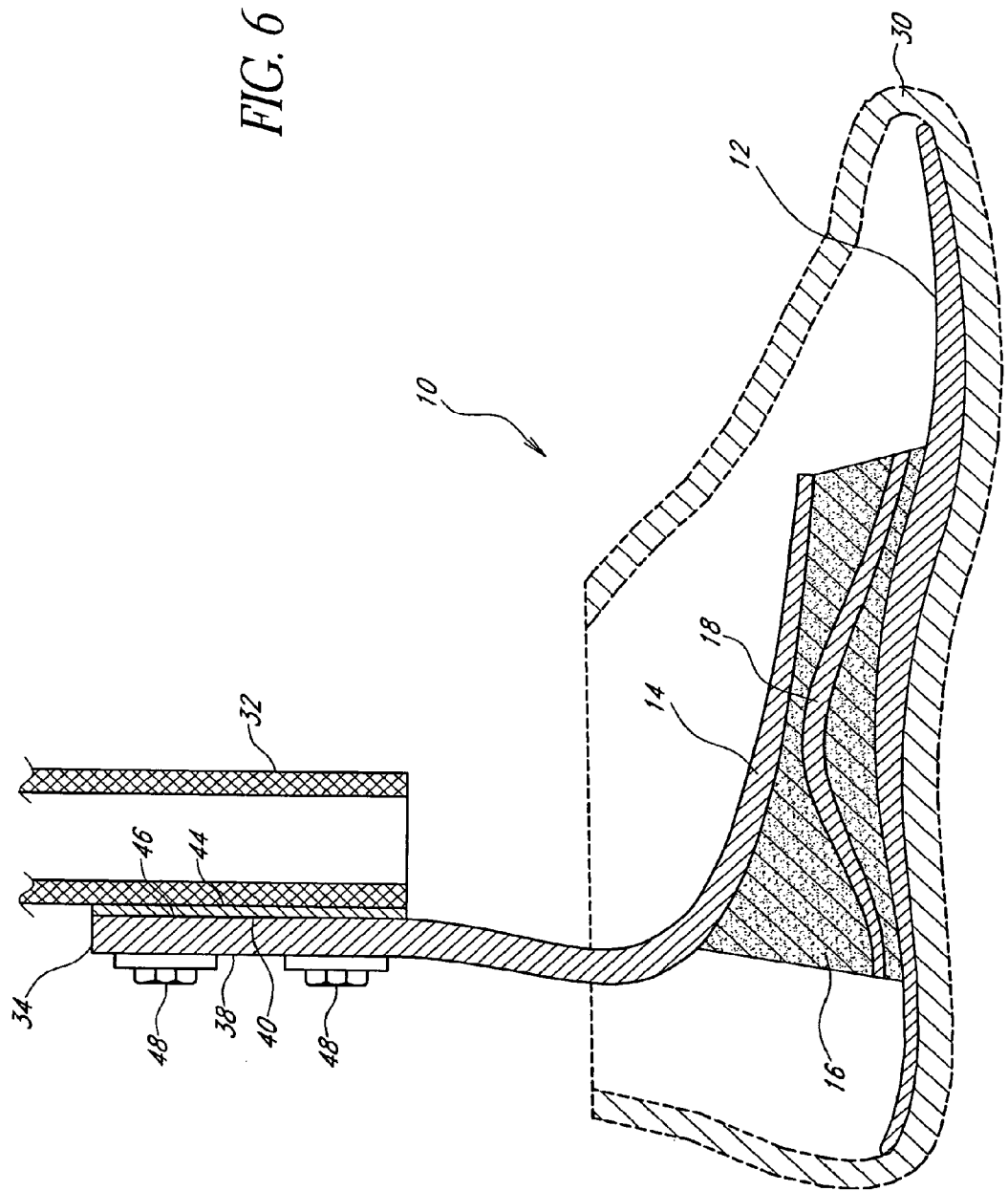

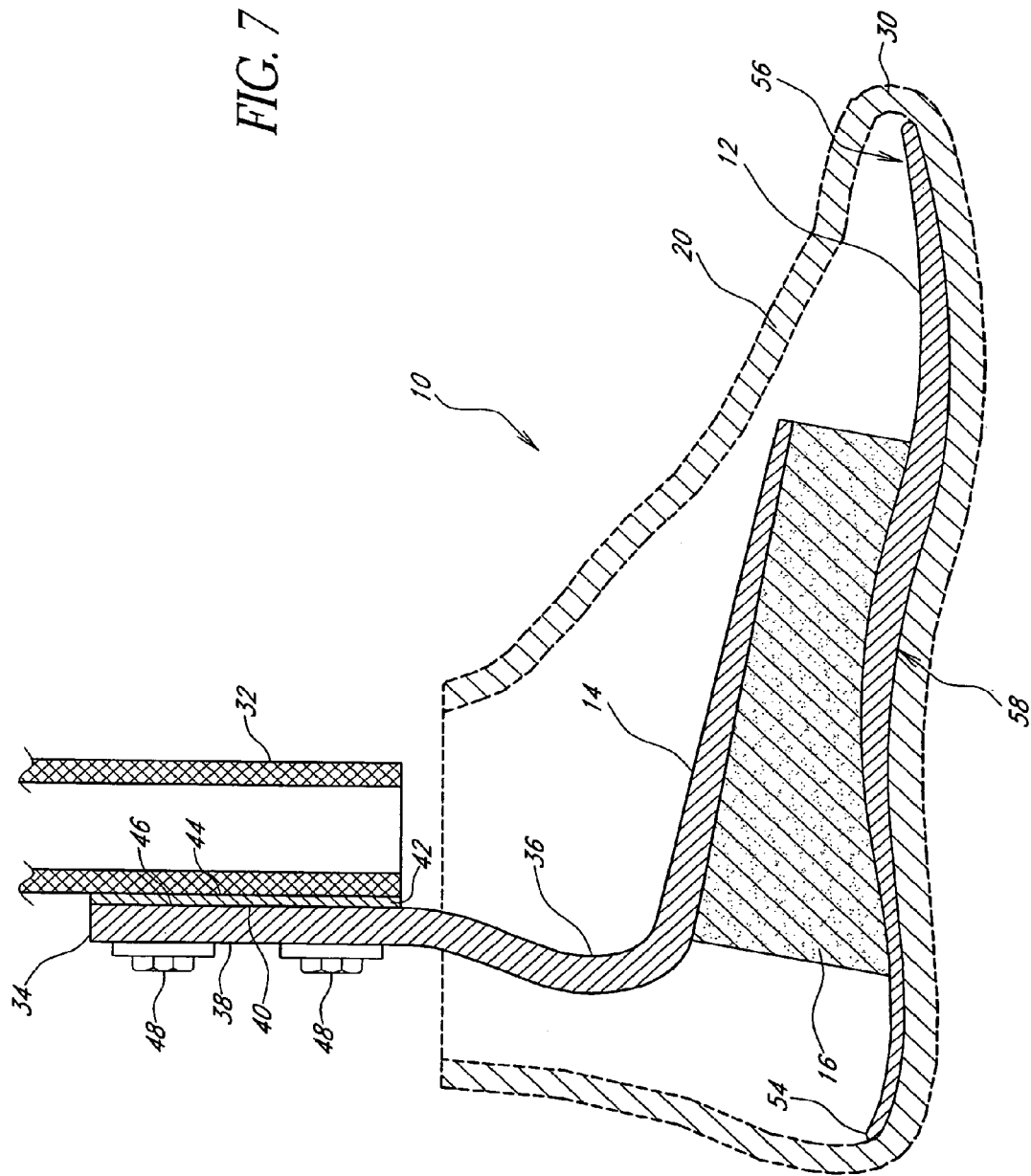

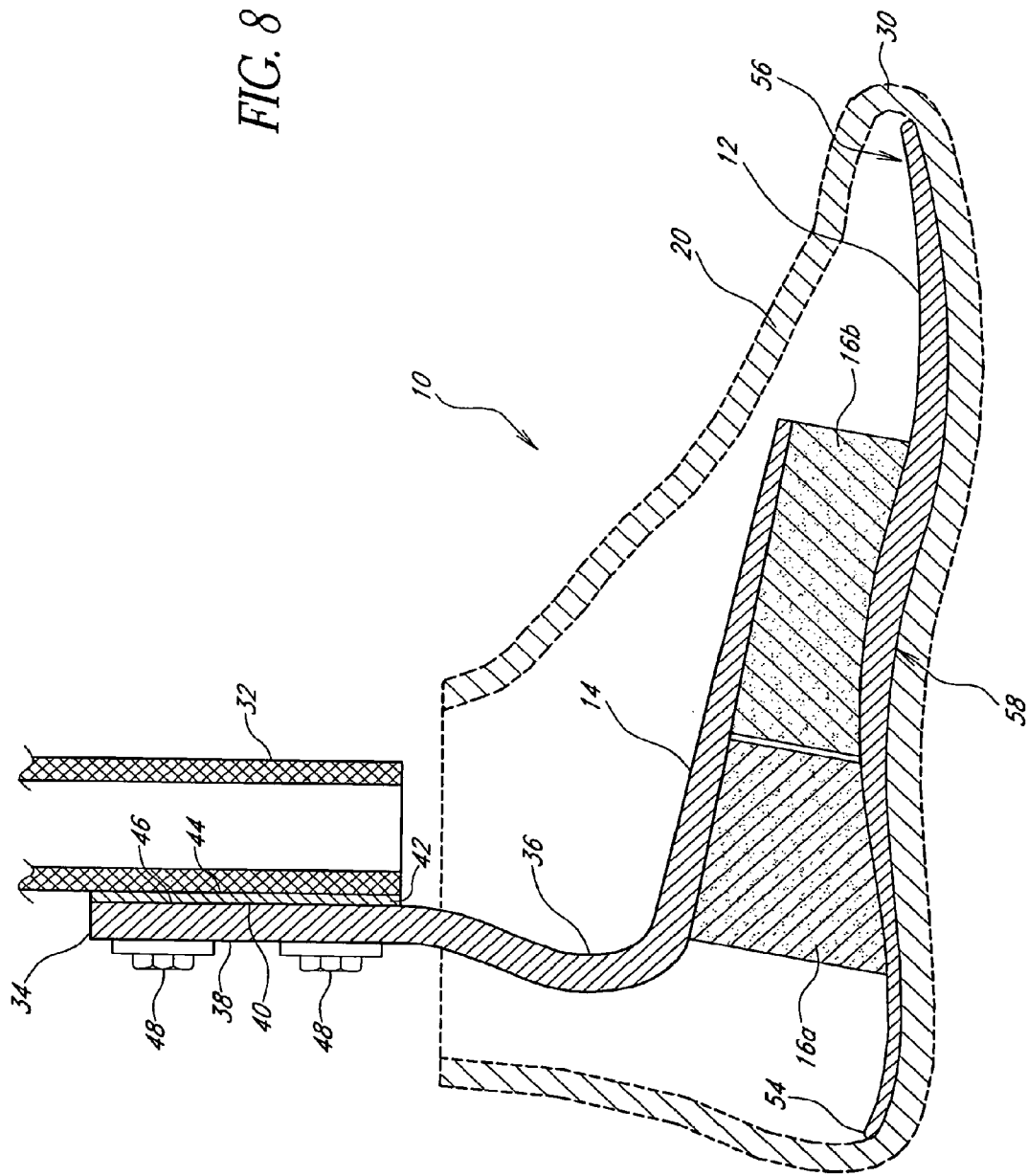

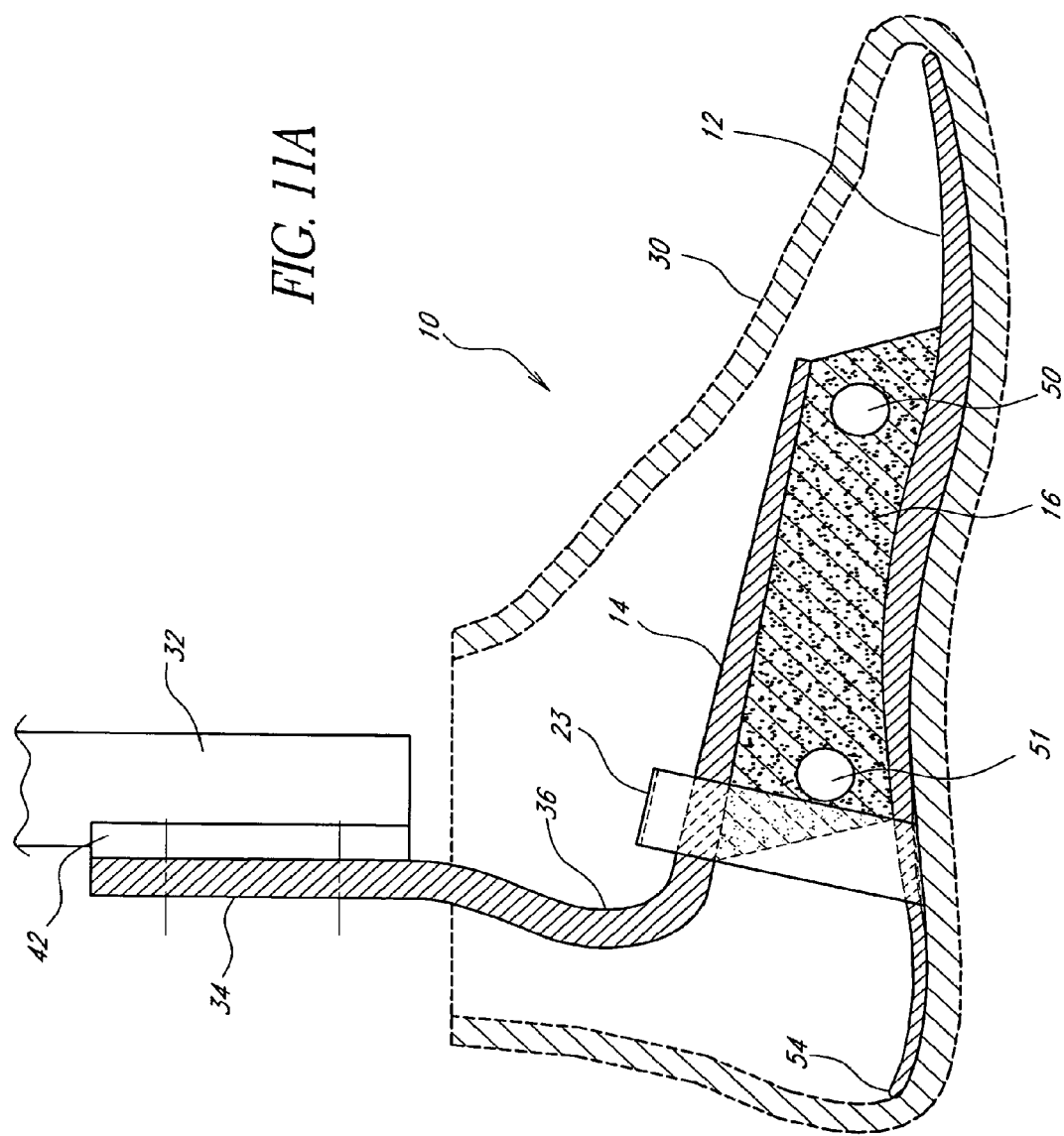

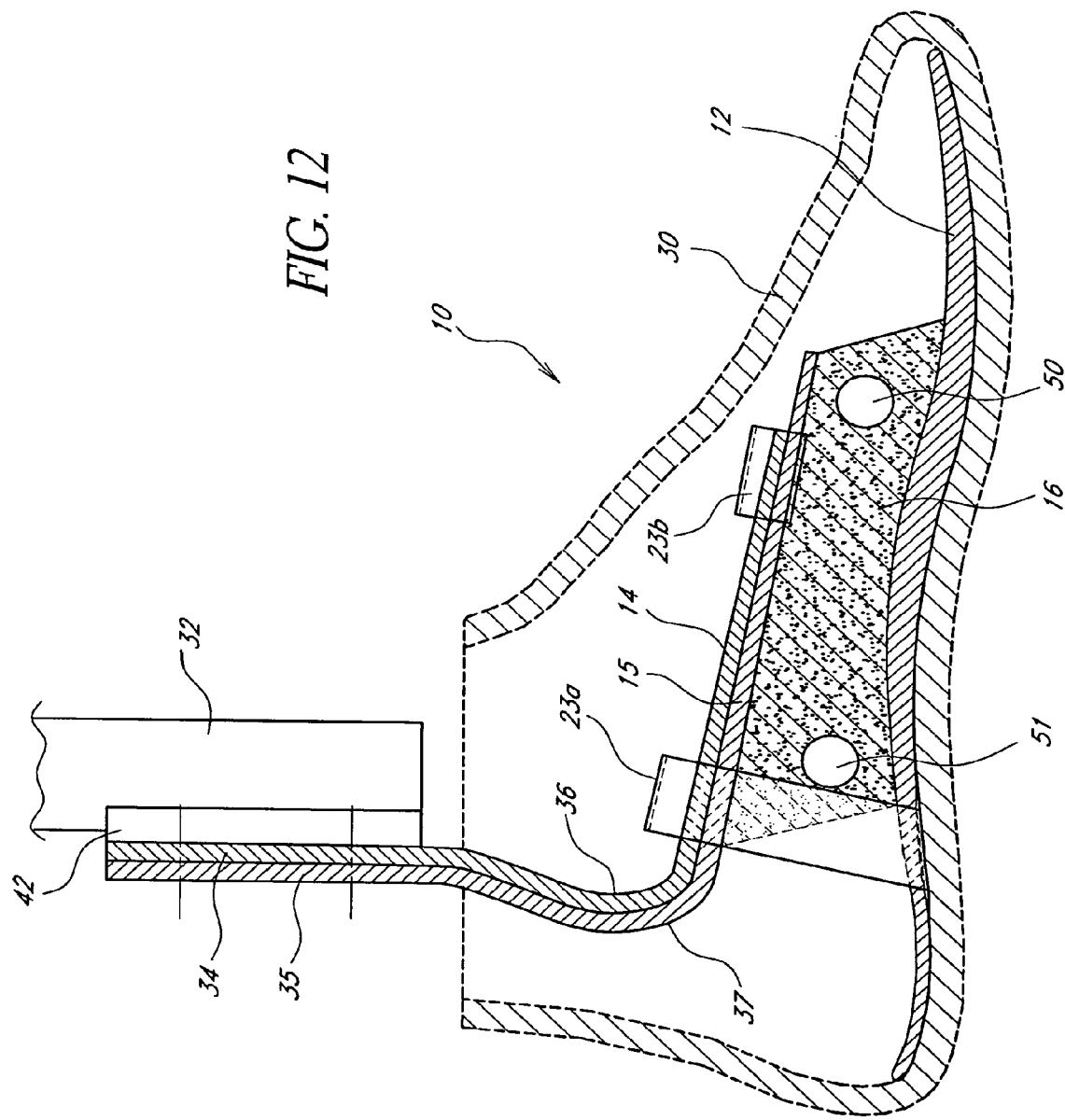

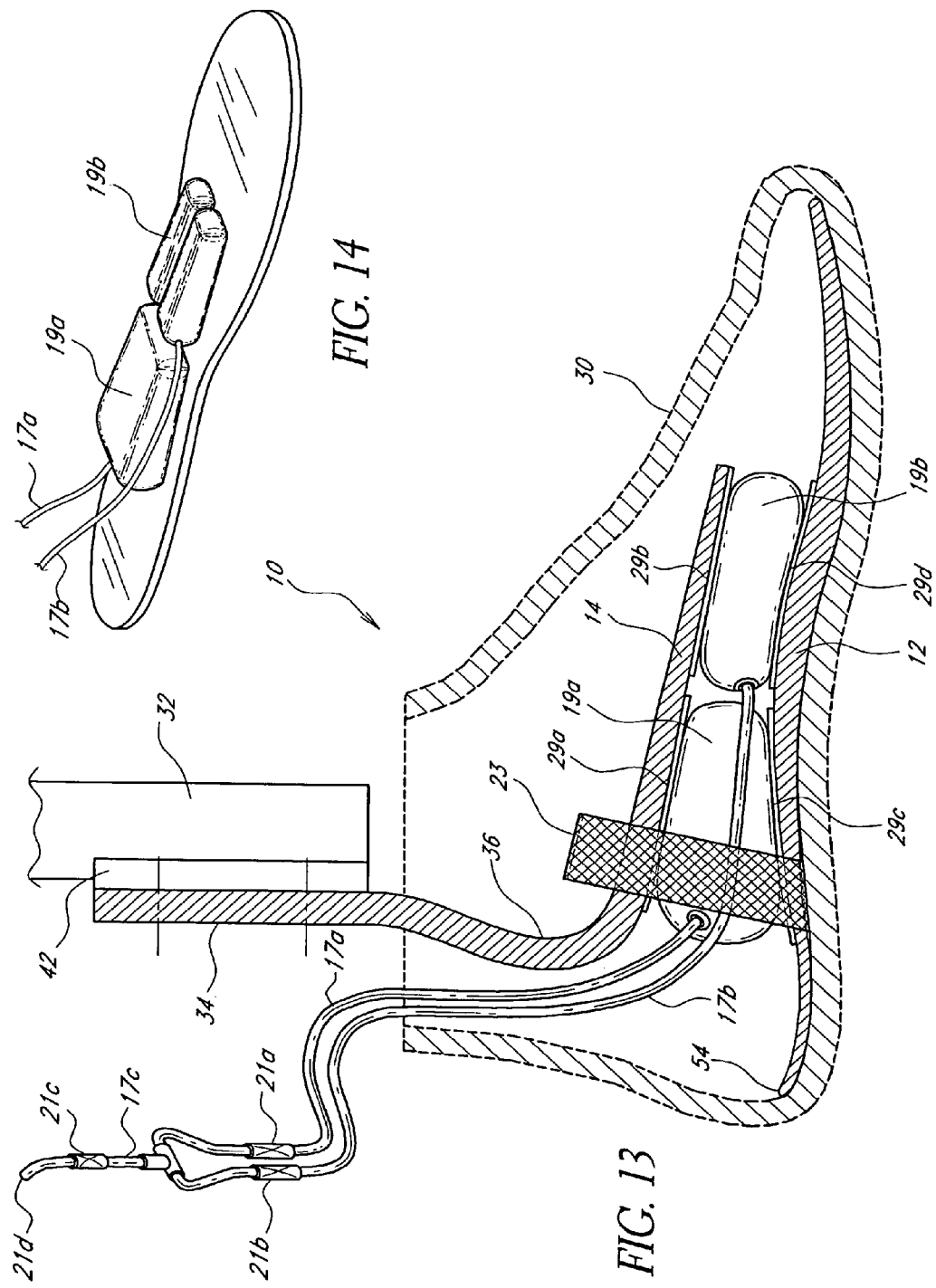

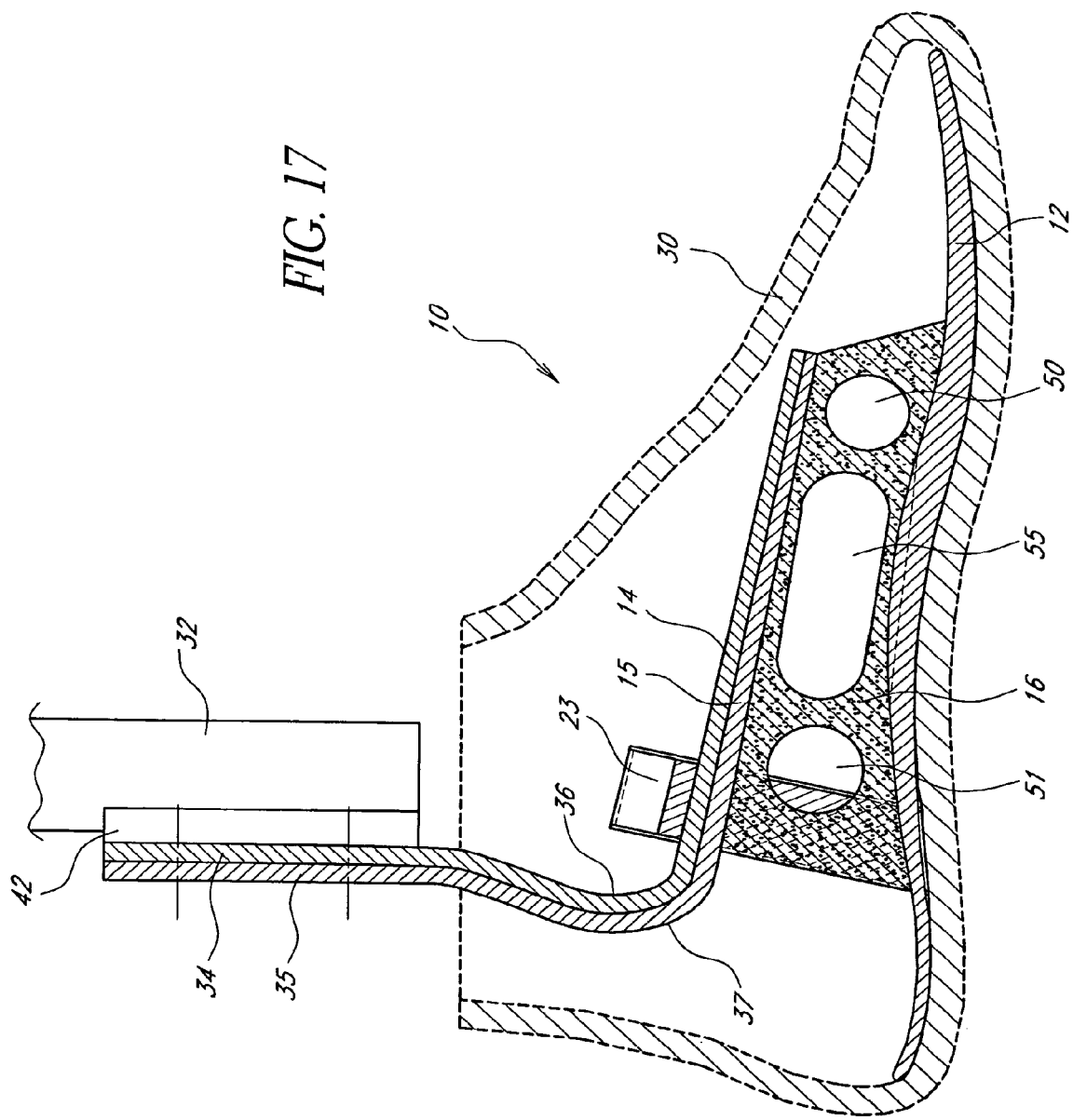

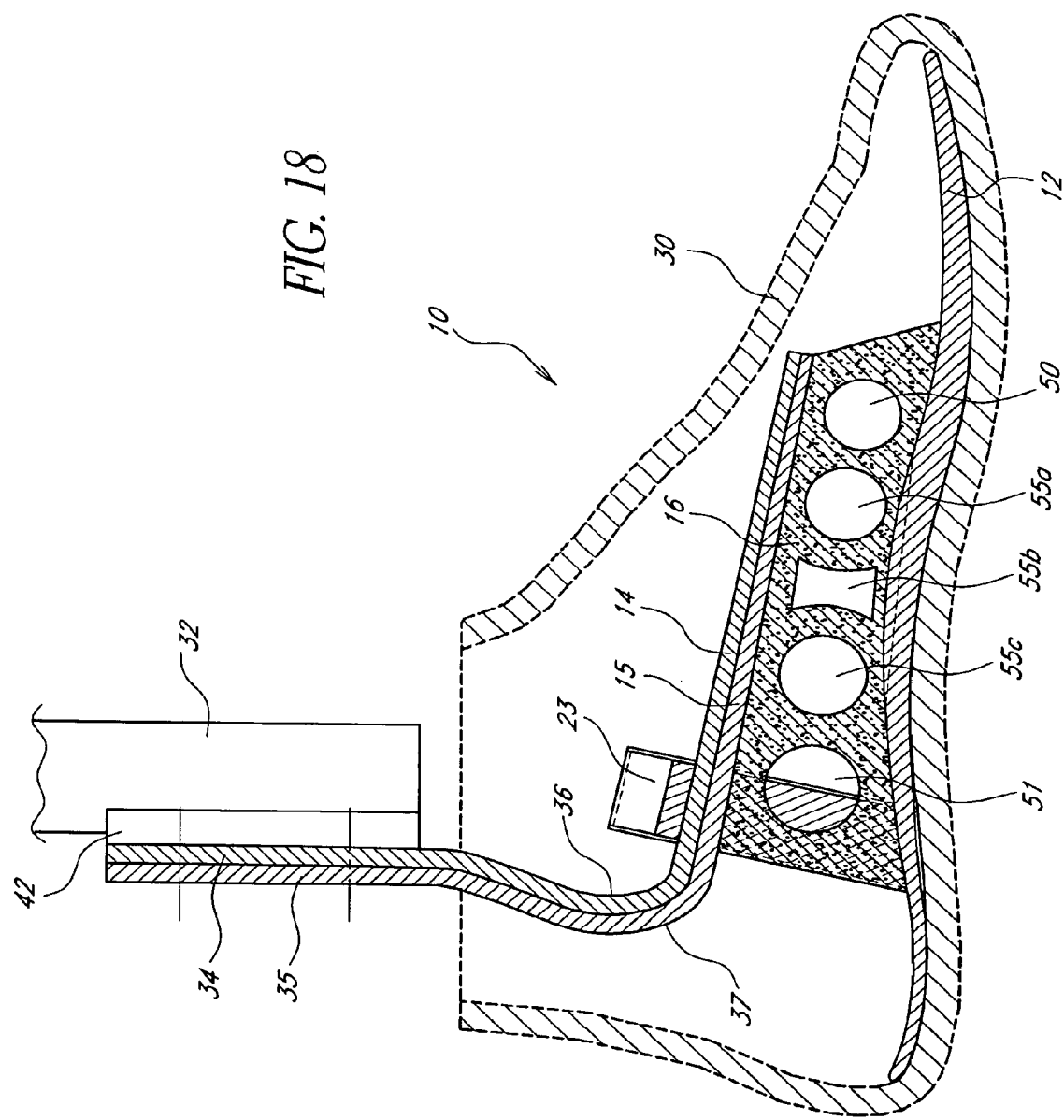

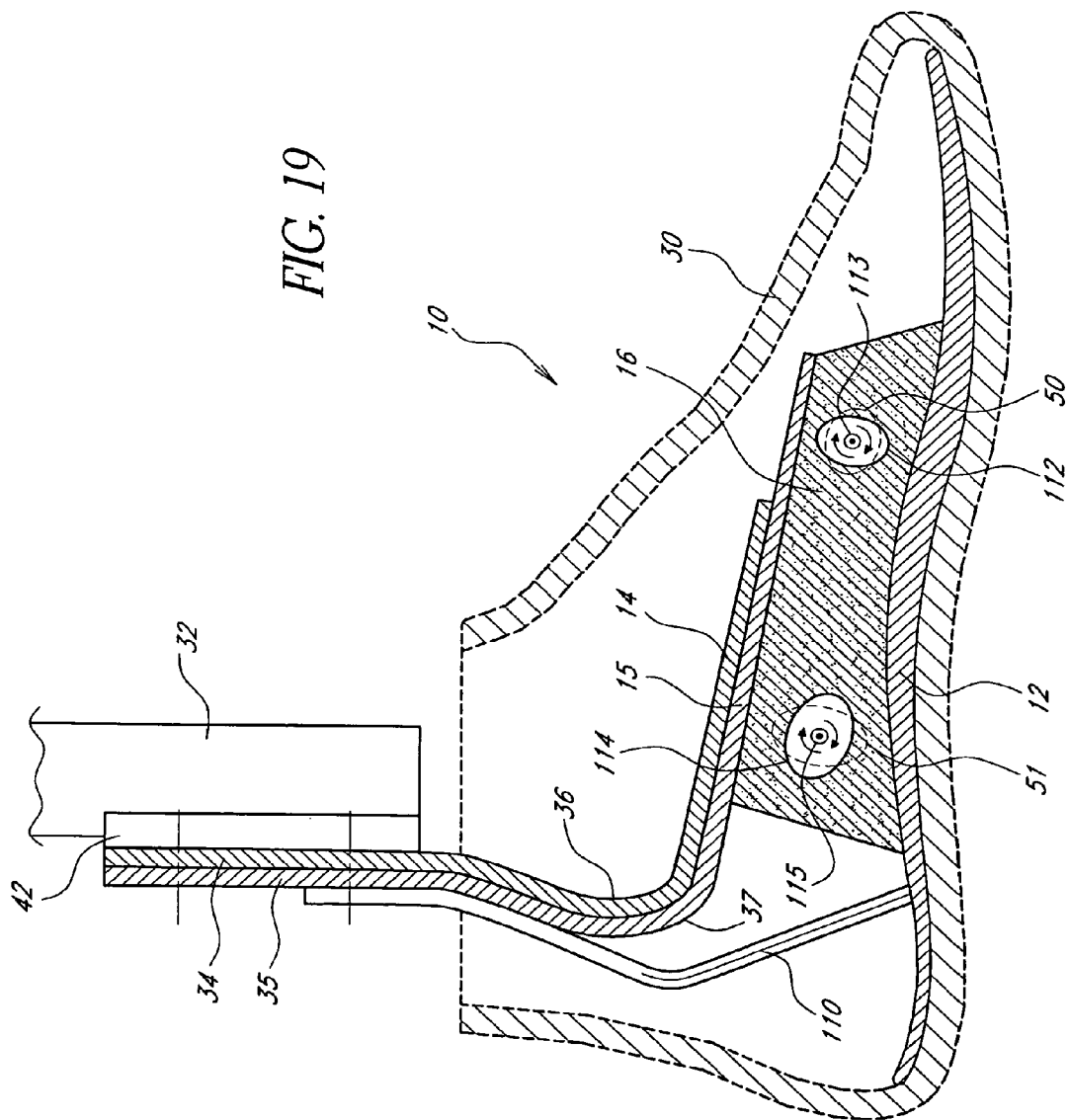

FOOT PROSTHESIS HAVING CUSHIONED ANKLE

CROSS-REFERENCE TO RELATED APPLICATIONS

This application is a continuation of copending application Ser. No. 11/868,457, filed Oct. 5, 2007, which is a divisional of application Ser. No. 10/776,123, filed Feb. 11, 2004, now U.S. Pat. No. 7,279,011, which is a divisional of application Ser. No. 09/698,489, filed Oct. 26, 2000, now U.S. Pat. No. 6,899,737.

BACKGROUND OF THE INVENTION

1. Field of the Invention

The present invention relates to prosthetic feet and, more particularly, to a simply constructed, low-profile prosthetic foot having enhanced performance characteristics.

2. Description of the Related Art

In the prosthetics market, the conventional SACH (solid-ankle, cushion-heel) foot has been the most widely prescribed artificial foot over the past 35 years. The SACH foot generally includes a solid ankle and cushioned heel foot mounted to a limb along an approximate hinge axis taken through the ankle. The SACH foot has been popular precisely for its simplicity, and thus economy, but includes certain drawbacks in terms of dynamic response characteristics. Specifically, the low end SACH feet do not provide much energy storage and release, as do more sophisticated prosthetic feet.

Most modern foot prostheses incorporate some form of energy storage element for storing and releasing walking energy. Conventionally, this might consist of a spring-loaded ankle joint comprising metal coil springs or, more commonly, rubber compliance members. Inexpensive foot prostheses have also been devised having essentially a solid rubber or foam ankle block for storing and releasing walking energy. Such an ankle block has been disclosed in my issued patent titled PROSTHESIS WITH RESILIENT ANKLE BLOCK, U.S. Pat. No. 5,800,569, the entirety of which is incorporated by reference. A solid, compressible ankle block may be secured between upper and lower support members to provide resilient compression and energy storage and release. The use of an ankle block member provides significant manufacturing and cost advantages. However, for certain applications it is difficult to attain a desired level of spring compliance and energy return characteristics using a solid ankle block due to the inherent limitations of the materials involved in terms of elasticity, viscosity and maximum compression.

SUMMARY OF THE INVENTION

One embodiment of the present invention provides a simple, inexpensive prosthetic foot incorporating an ankle block having selectable compliance and energy return characteristics that may be varied over a wider range to accommodate the different weight, height and activity level of amputees. The ankle block is formed of compressible material having desired compliance and energy return characteristics. The ankle block is sandwiched between a foot element and an ankle element. One or more spring inserts are embedded inside the ankle block to increase the rigidity of the prosthetic foot and to improve the degree of energy storage and return. The shape of the spring inserts is preferably one that supports compression during relative angular rotation of the ankle plate and foot plate elements, such as during toe and heel roll, and also vertical compression, such as in response to vertical shock loads.

In one aspect of the present invention, a basic prosthetic foot is provided having enhanced performance characteristics generally comprising a lower foot plate, an upper ankle plate, a foam ankle block joining the two plates, and a spring element embedded in the ankle block. Both the foot plate and the ankle plate are constructed of strong, flexible material, preferably a laminate of composite material. The foot plate is sized approximately equal to a human foot being replaced, while the ankle plate has a similar width, but has a shorter length than the foot plate. The ankle block has a length and width approximately equal to the ankle plate and is aligned therewith. The spring element comprises two relatively flat carbon fiber composite members secured at their middle and separated at their ends. This gives the spring element a preferable shape of a bow tie or double wishbone. Preferably, an attachment member couples the ankle plate to a stump or lower-limb pylon of the wearer. During walking, the combination of the resilient ankle block with embedded spring element and flexible plates provides a smooth rollover from a heel-strike to a toe-off position.

In another aspect, the ankle block of a prosthetic foot may be provided with cylindrical openings both in the fore and aft positions of the ankle block. These openings enable the placement of additional inserts or stiffeners to give the block a desired rigidity. In a preferred embodiment, the foot element also has a tapered thickness. Further, the foot element comprises uplifted heel and toe ends and an arch region therebetween.

In another aspect, a prosthetic foot is provided comprising a foot plate element, at least one ankle plate element and an ankle block sandwiched between the foot plate element and the ankle plate element. The foot plate element has a length approximately equal to the length of a human foot, and comprises a resilient material capable of flexing along its length. The at least one ankle plate element has a length substantially shorter than the foot plate element. The ankle block comprises a relatively soft, compressible material and provides substantially the sole means of support and connection between the foot plate element and the ankle plate element. At least one opening extends through the ankle block with a substantially transverse orientation relative to a forward walking motion. The foot plate element and the ankle block flex in a cooperative manner to provide substantially smooth and continuous rollover transition from heel-strike to toe-off.

In another aspect, a prosthetic foot comprises a lower foot plate, an upper ankle plate disposed above and generally over the lower foot plate and being spaced therefrom, and a plurality of inflatable bladders disposed between the upper ankle plate and the lower foot plate and separating the upper plate from the lower plate. The bladders provide substantially the sole means of support between the foot plate and the ankle plate. The foot plate and the bladder flex in a cooperative manner to provide substantially smooth and continuous rollover transition from heel-strike to toe-off.

In another aspect, a prosthetic foot for connecting to a pylon of an amputee is provided. The prosthetic foot comprises a foot plate element having a length approximately equal to the length of a human foot, an ankle plate having a length substantially shorter than the foot plate element, and at least one inflatable bladder between the ankle plate element and the foot plate element. The foot plate element comprises a resilient material capable of flexing along its length. The at least one inflatable bladder provides substantially the sole means of support and connection between the foot plate element and the ankle plate element. A fluid pump generates fluid pressure based on the movement of the amputee onto the pylon. A fluid pathway directs fluid into the at least one inflatable bladder.

In another aspect, a pump system for a prosthetic foot is provided. The system comprises at least one inflatable bladder, a syringe including a plunger and a cylinder, a fluid pathway connecting the syringe to the at least one inflatable bladder, and a first pylon and a second pylon telescopingly engaged. The plunger is connected to the first pylon and the cylinder is connected to the second pylon, such that relative movement between the first and second pylon moves the plunger in and out of the cylinder to generate pressure within the at least one inflatable bladder.

In another aspect, a prosthetic foot is provided comprising an inner pylon and an outer pylon that are telescopingly engaged. A compressible member is positioned in a chamber defined between the inner and outer pylons. The inner pylon moves relative to the outer pylon upon the application and release of a compressive force onto the prosthetic foot. A fluid line is also provided in communication with the chamber. At least one inflatable bladder is in communication with the fluid line, and fluid pressure is generated in the at least one inflatable bladder based on the relative movement between the inner and outer pylons. In another aspect, a prosthetic foot comprises a foot plate element comprising a resilient material capable of flexing along its length, and at least one ankle plate element. An ankle block comprising a relatively soft, compressible material is sandwiched between the ankle plate element and the foot plate element. The ankle block provides substantially the sole means of support and connection between the foot plate element and the ankle plate element. At least one opening extends through the ankle block with a substantially transverse orientation relative to a forward walking motion. At least one cam is inserted into the at least one opening, the cam being rotatable to locally adjust the stiffness of the ankle block.

In another aspect, the prosthetic foot having a foot plate element, at least one ankle plate element and an ankle block sandwiched therebetween, includes a first and second chamber extending through the ankle block. The first chamber is positioned in a fore portion of the block and the second chamber is positioned in a rear portion of the block, the first and second chambers being oriented generally transverse to a forward walking motion. First and second stiffeners are positioned in the first and second chambers, respectively, the first and second stiffeners being moveable within each of said chambers.

In another aspect, a prosthetic foot is provided comprising a foot plate element comprising a resilient material capable of flexing along its length, and at least one ankle plate element. An ankle block comprising a relatively soft, compressible material is sandwiched between the ankle plate element and the foot plate element. The ankle block provides substantially the sole means of support and connection between the foot plate element and the ankle plate element. The ankle block includes a wedge cut-out in a rear portion of the ankle block. In one embodiment, the prosthetic foot further comprises a wedge piece inserted into the wedge cut-out.

In another aspect, the prosthetic foot comprising a foot plate element, at least one ankle plate element and an ankle support member sandwiched therebetween is further provided with a strap connecting the ankle plate element to the foot plate element. The strap is positioned behind the ankle block relative to a forward walking motion and is capable of adjusting the relative flexing properties between said ankle plate element and said foot plate element.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 6 is a cross-sectional view of an alternative embodiment of a prosthetic foot of the present invention incorporating a modified spring element.

FIG. 7 is a cross-sectional view of another alternative embodiment of a prosthetic foot of the present invention incorporating a modified ankle block.

FIG. 8 is a cross-sectional view of another alternative embodiment of a prosthetic foot of the present invention incorporating a modified ankle block.

FIG. 11A is a partial cross-sectional view of another alternative embodiment of a prosthetic foot of the present invention incorporating cylindrical slots.

FIG. 12 is a partial cross-sectional view of another alternative embodiment of a prosthetic foot of the present invention incorporating dual ankle plates and cylindrical slots.

FIG. 13 is a partial cross-sectional view of another alternative embodiment of a prosthetic foot of the present invention incorporating toe and heel air bladders.

FIG. 14 is a perspective view of the heel and toe bladders of FIG. 13.

FIGS. 17 and 18 are partial cross-sectional view of additional alternative embodiments of a prosthetic foot of the present invention incorporating chambered urethane.

FIG. 19 is a partial cross-sectional view of another alternative embodiment of a prosthetic foot of the present invention incorporating rotatable cams.

DETAILED DESCRIPTION OF THE PREFERRED EMBODIMENTS

Figure 1:
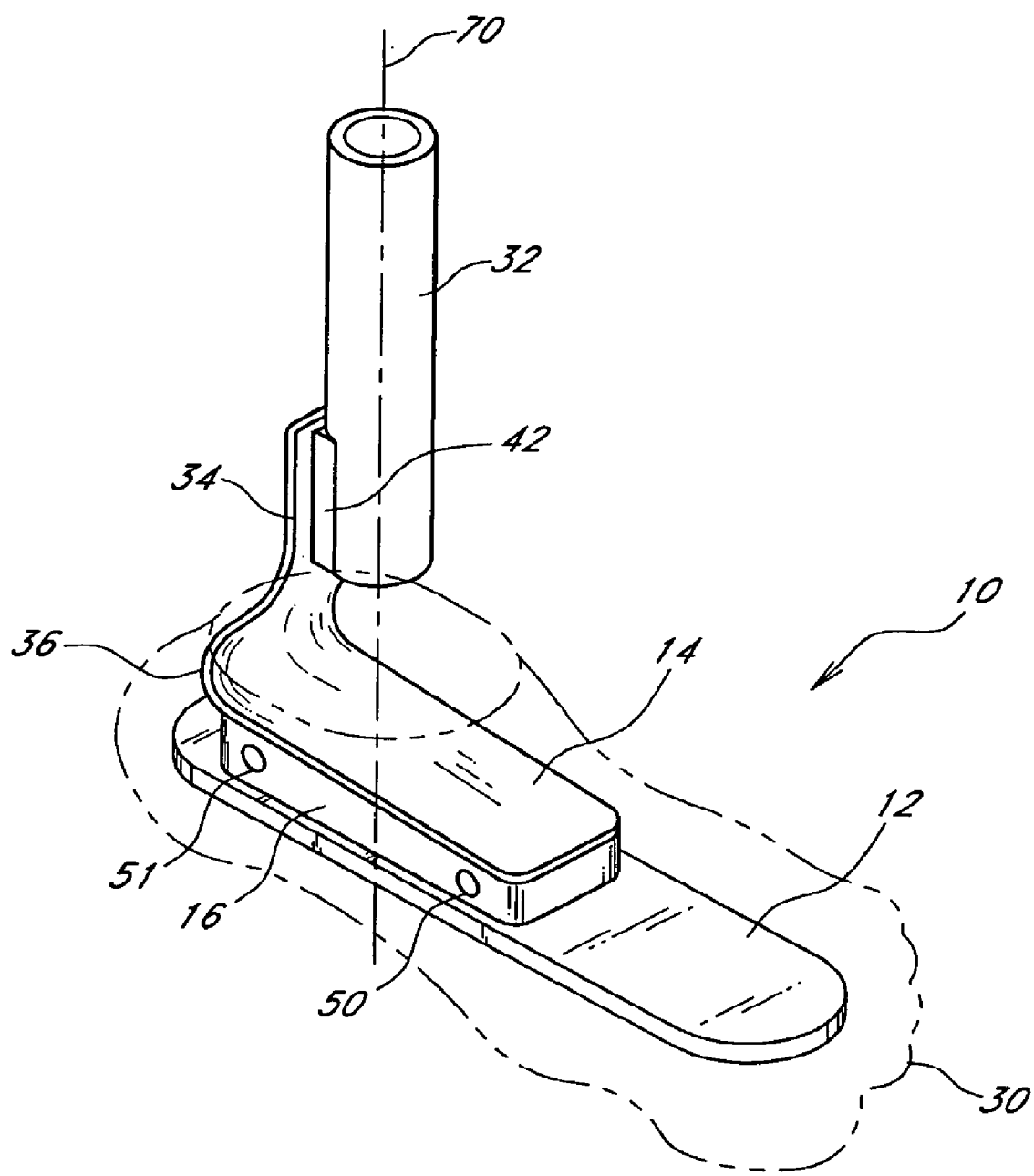
FIG. 1 is a perspective view of a prosthetic foot in one embodiment of the present invention.
Figure 2:
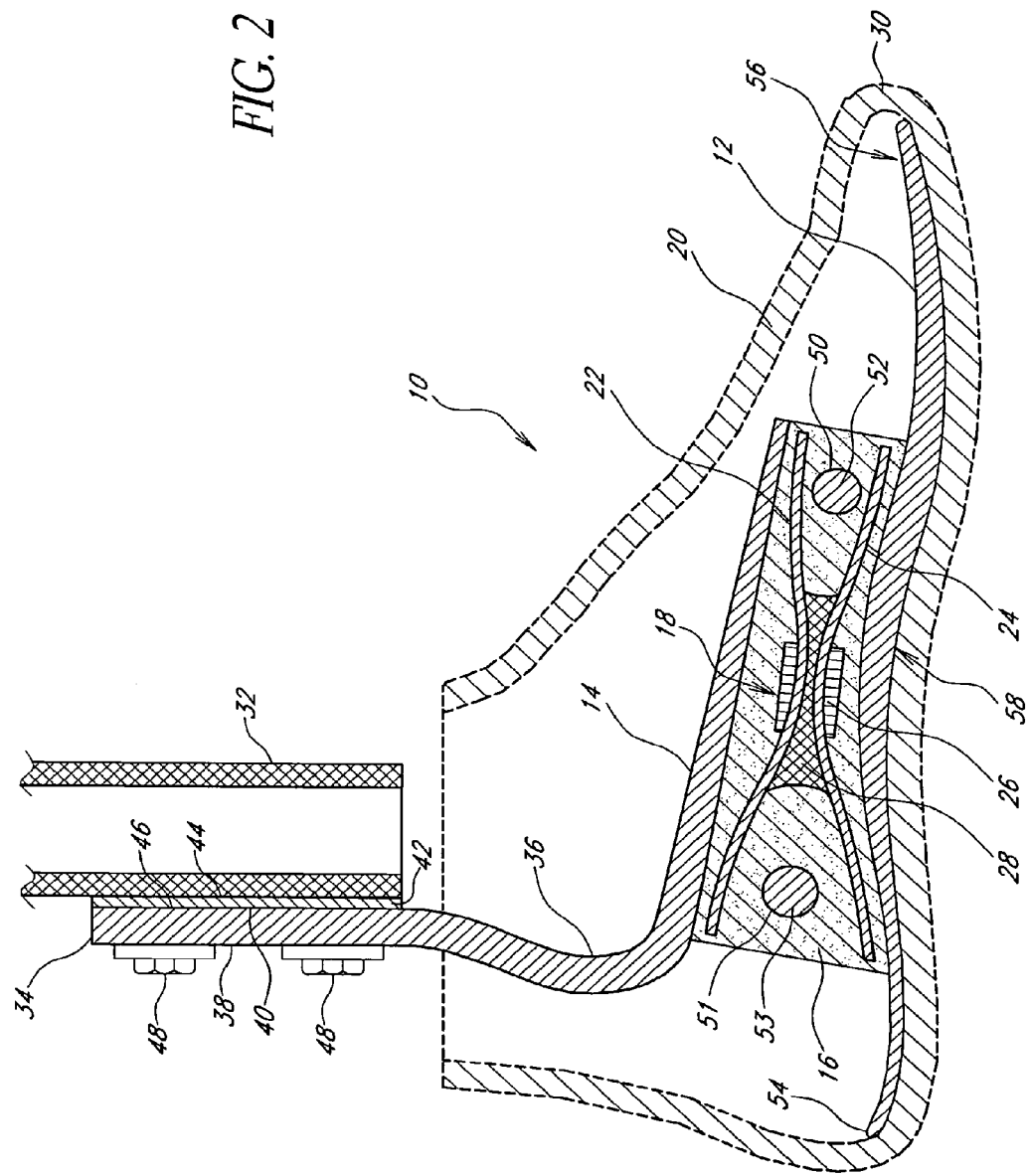
FIG. 2 is a cross-sectional view of a prosthetic foot in one embodiment of the present invention.

With reference to FIGS. 1 and 2, a first embodiment of a prosthetic foot 10 of the present invention is shown in a perspective view and a cross-sectional side view, respectively. The prosthetic foot 10 generally comprises a lower foot plate 12, an upper, smaller ankle plate 14, an ankle layer or block 16 made of resilient material, connecting the foot plate 12 to the ankle plate 14, and a spring element 18 embedded within the ankle block 16. The foot plate 12 has a length and width roughly equal to the approximate length and width of the particular wearer's amputated foot and sized to fit within an outer, flexible cosmesis 30, shown in phantom. The ankle plate 14 and the resilient ankle block 16 have approximately the same horizontal cross-sectional size. The ankle plate 14, ankle block 16, and spring element 18 are centered transversely with respect to and are generally positioned over the back half of the foot plate 12. The ankle block 16 is sandwiched between the foot plate 12 and the ankle plate 14 and is preferably glued or bonded to both plates using polyurethane adhesive or other known securement technologies.

Figure 3:
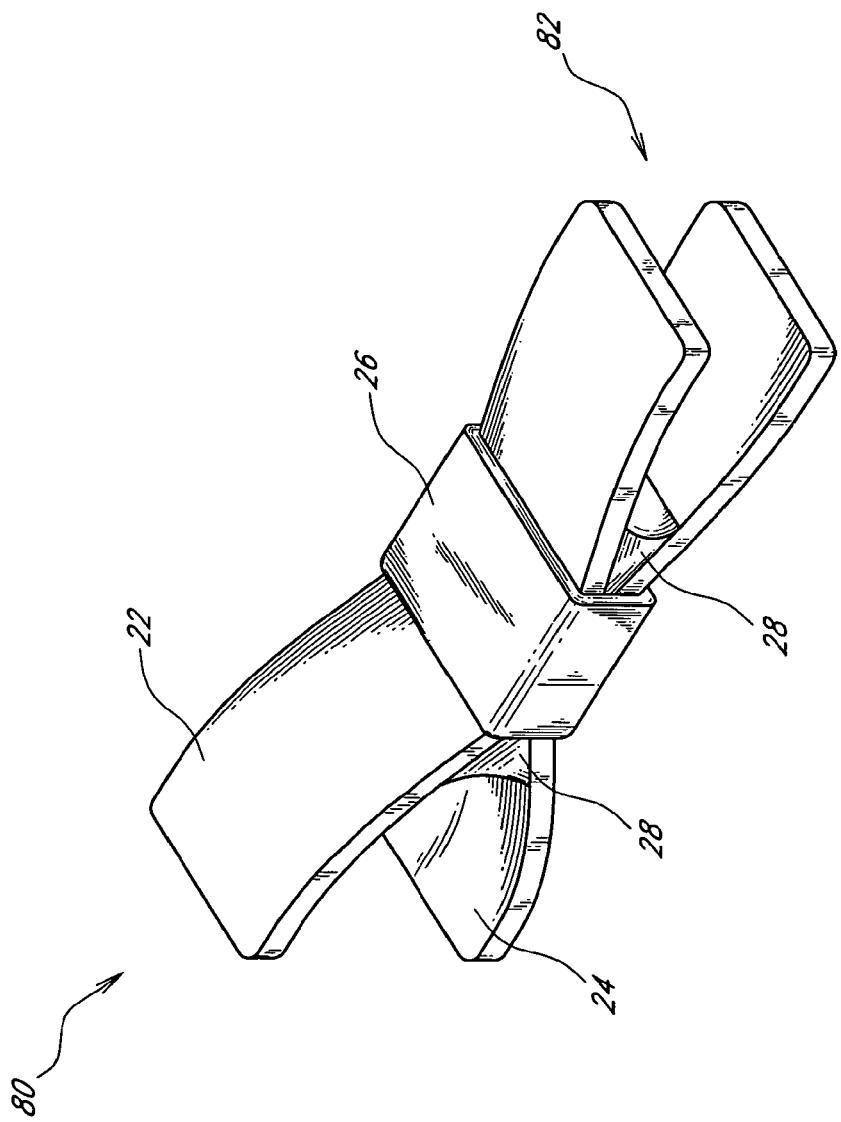
FIG. 3 is a perspective view of a spring element embedded in the ankle block in one embodiment of the present invention.

The spring element 18 is a resilient support member inserted within the resilient ankle block 16. As shown in FIG. 3, the spring element 18 is preferably comprised of upper and lower plate-like members 22 and 24, each of which is relatively flat and has a substantially rectangular vertical projection. These members are secured at their center by a fastener 26 and separated at ends 80 and 82. The upper member 22 preferably has a curvilinear concave upward shape, while the lower member 24 preferably has a curvilinear concave downward shape. This gives the spring element 18 a substantially double wishbone or bow tie shape.

As shown in FIG. 1, the spring element 18 is completely embedded within the ankle block 16 so as not to be visible from the outside. Referring to FIG. 2, the spring element 18 extends substantially longitudinally across the length of the ankle block 16, and has a width substantially equal to the width of ankle block 16. The fastener 26 may comprise bolts, a weld, or any other fastening means as would be known to those skilled in the art. In the preferred embodiment, the fastener 26 is a strap which is laminated around the center portion of the two members 22, 24. A wedge member 28, preferably of a resilient elastomer, is placed between the two plate members 22, 24 to protect the inner surfaces of the members and to provide additional support to the spring element 18. The wedge 28 acts to provide leverage between the two plate members 22, 24, and enables adjustment of the flexing characteristics of the spring element 18, if desired. Alternatively, it may be bonded permanently in place or formed integrally with one or both of the plate members 22, 24, as desired. Although the spring element 18 has been described as having a double wishbone or bow tie configuration, other shapes and sizes may be appropriate for providing support to the ankle block 16. Furthermore, more than one spring element may be provided in the ankle block to provide support and energy return to the prosthetic foot 10.

As can be seen in FIGS. 1 and 2, the prosthetic foot 10 further comprises a pylon member 32 which can be secured to the stump of the amputee (not shown) and extends relatively downward therefrom in a generally vertical direction. The pylon member 32 in the preferred embodiment is of tubular construction having a substantially equal moment of inertia in all directions to restrict bending in all directions. The tubular member 32 is also preferably hollow so that it is relatively light in weight and utilizes less material which reduces the cost of production. The pylon member 32 is dimensioned so as to be interchangeable with a standard 30 mm pylon. Other configurations which impart rigidity, such as rectilinear cross sections having relatively larger moments of inertia about one or both transverse axes can also be utilized to obtain the benefits discussed herein. A centerline 70 through pylon 32, shown in FIG. 1, defines the downward direction of the application of force.

As shown in FIGS. 1 and 2, the ankle plate 14 is secured to the pylon member 32 through a vertically oriented upper attachment member 34. The upper attachment member 34 is attached to a curvilinear ankle section 36, which is connected to the ankle plate 14. Preferably, these three pieces are monolithically formed with one another for optimum strength and durability. The attachment member 34 has a rearward surface 38, as shown in FIG. 2, and a forward surface 40 substantially parallel thereto. The attachment member 34 is substantially rigid and capable of sustaining torsional, impact and other loads impressed thereupon by the prosthesis. In addition, the inherent rigidity of attachment member 34 prevents it from being distorted in any substantial way and causes the effective transmission of the aforesaid loads imposed thereupon to a suitable ancillary prosthetic pylon 32.

With reference to FIG. 2, the attachment member 34 is in the preferred embodiment vertically oriented so that it may be secured to the pylon member 32. A coupling device 42 is positioned at the lower end of the pylon member 32 which provides a flat surface upon which the vertical attachment member 34 can be secured. The coupling device 42 has one attachment surface 44 which mates with the cylindrical outer surface of the pylon member 32 and a second substantially flat attachment surface 46 which mates with the attachment member 34. In the preferred embodiment, attachment surface 44 is curved to mate with the outer surface of the tubular pylon member 32, and attachment surface 46 is flat to accommodate the forward surface 40 of the attachment member 34.

Desirably, the coupling device 42 is welded or bonded to the pylon member 32 and has two holes (not shown) into which two bolts 48 can be inserted and secured. The attachment member 34 also has two holes (not shown) which align with the holes on the coupling device to place and secure the two bolts 48 through the attachment member 34 and the coupling device 42. Other methods of securing the pylon member to the foot portion are contemplated, such as those disclosed in my prior issued U.S. Pat. No. 5,514,186, the entirety of which is incorporated by reference, as well as those utilizing integrally formed constructions.

As stated, the attachment member 34 monolithically formed with the ankle plate 14 is vertically aligned so that it extends relatively downward from the coupling device 42 on the pylon member 32. As shown in FIG. 2, the thickness of the attachment member 34 along this vertical section is relatively greater than the thickness of the ankle plate 14 substantially horizontally aligned along the foot portion. The attachment member 34 is also made relatively thicker to support the vertical load imposed on the prosthetic device as well as to restrict undue bending at this juncture. The entire upper vertically-aligned section of attachment member 34 is preferably of substantially uniform thickness and width.

The tubular pylon member 32 is preferably removable from the prosthetic device such that the pylon member can be replaced without replacing the remainder of the prosthetic device. This permits Applicant's invention to be utilized in a broader range of applications. For instance, the tubular member of Applicant's invention can be cut and adapted for use by amputees having different stump lengths including growing amputees. The prosthetist merely needs to cut a standard tubular pylon to the appropriate length. Moreover, this eliminates the need to manufacture as a part of the prosthesis a long rigid leg section. Thus, fewer materials are needed to manufacture the prosthesis of Applicant's invention resulting in reduced manufacturing costs.

The preferred embodiment further comprises cylindrical slots or openings 50, 51 in the fore and aft portions of the ankle block 16, respectively, as shown in FIG. 2, to accommodate insertion of stiffeners 52, 53. The cylindrical openings 50, 51 are disposed horizontally in a direction generally transverse to a forward walking motion, and between upper and lower plate members 22 and 24. Stiffeners 52, 53 can be removably placed in these openings to provide additional support and rigidity to the prosthetic foot 10, and also to modify the spring characteristics of the prosthetic foot. For instance, additional energy storage and return can be provided for a more active amputee by inserting stiffeners 52, 53 into ankle block 16 having a higher spring constant. On the other hand, when more control is desired, stiffeners with a lower spring constant may be inserted to produce an ankle block 16 with greater dampening characteristics. Alternatively, the cylindrical openings 50, 51 may remain empty, thereby making the compliance characteristics dependent solely on the ankle block 16 and the spring element 18.

Preferred Materials and Fabrication

Both the foot plate 12 and the ankle plate 14 are preferably formed of a flexible material so that flexing of the plates tends to relieve extreme shear stresses applied to the interfaces between the ankle block 16 and the plates 12, 14. Both the foot plate 12 and the ankle plate 14 are preferably constructed of fiberglass which provides strength and flexibility. The preferred material for the ankle plate 14 and the foot plate 12 is a vinyl ester based sheet molding compound, such as Quantum #QC-8800, available from Quantum Composites of Midland, Mich. Alternatively, the plates may be formed by a plurality of lamina embedded in a hardened flexible polymer. In other arrangements, the plates may be formed of other materials such as carbon fiber composites as may be apparent to one skilled in the art. The desirable properties of the plates are that they are relatively resilient so as to withstand cracking upon application of repeated bending stresses yet have sufficient flexibility to enhance the performance characteristics felt by the wearer in conjunction with the properties of the resilient ankle block. The pylon member 32 is preferably made of a stiff material such as a laminate of fiber reinforced composite. Stiffness in the pylon member 32 can also be provided by a stiffer and more dense material.

The ankle block 16 is sandwiched between the foot plate 12 and the ankle plate 14 as shown in FIGS. 1 and 2 and is preferably bonded to both plates. The ankle block is preferably formed of urethane, rubber or other suitable material having desired compliance and energy return characteristics. A preferred material for the ankle block is expanded polyurethane foam such as cellular Vulkolka☐ Pur-Cell No. 15-50, with a density of approximately 500 kg/m$^3$ as available from Pleiger Plastics Company of Washington, Pa. Alternatively, the ankle block 16 may be molded or fabricated from a wide variety of other resilient materials as desired, such as natural or synthetic rubber, plastics, honeycomb structures or other materials. Cellular foam, however, provides a high level of compressibility with desirable visco-elastic springiness for a more natural feeling stride without the stiffness drawbacks and limited compression associated with solid elastomeric materials. Furthermore, the cellular nature of a foam block makes it lighter than solid elastomers. Foam densities between about 150 and 1500 kg/m$^3$ may be used to obtain the benefits of the invention taught herein.

The spring element 18 is preferably made from a highly resilient material that is capable of supporting compression during relative angular rotation of the upper and lower members 12 and 14, such as during toe and heel roll, and also vertical compression such as in response to vertical shock loads. One preferred material is carbon fiber composites such as woven fiber mats and chopped fiber in an epoxy matrix. However, other materials with similar strength and weight characteristics will be known to those skilled in the art and may be used with efficacy. For instance, other filament types may be used, such as glass, Kevlar and nylon by way of example, to ensure lightweight and structural and dynamic characteristics consistent with the needs of a particular amputee. The wedge 28 may be fabricated from a wide variety of resilient materials, including natural and synthetic rubber, elastomeric polyurethane, or the like.

The ankle block 16 containing spring element 18 may be fabricated by injecting a polyurethane elastomer into a mold allowing it to cure. The spring element 18 may be inserted into the mold prior to injection of the polyurethane so that during curing, the polyurethane bonds to the spring member. Cylindrical slots or openings 50, 51 for insertion of stiffeners 52, 53 may be provided in ankle block 16 by inserting cylindrical plugs into the block prior to injection of polyurethane. Alternatively, openings may be provided in the block after curing simply by cutting or drilling away portions of the ankle block.

The stiffeners provided in the openings are preferably tubes of foam material having a density chosen according to desired compliance characteristics. A preferable material is expanded polyurethane having a foam density between about 150 and 1500 kg/m$^3$. More preferably, a density of about 250 to 750 kg/m$^3$ is preferred to provide adequate adjustment of the energy storage and return characteristics of the foot.

Preferred Dimensions

Figure 4:
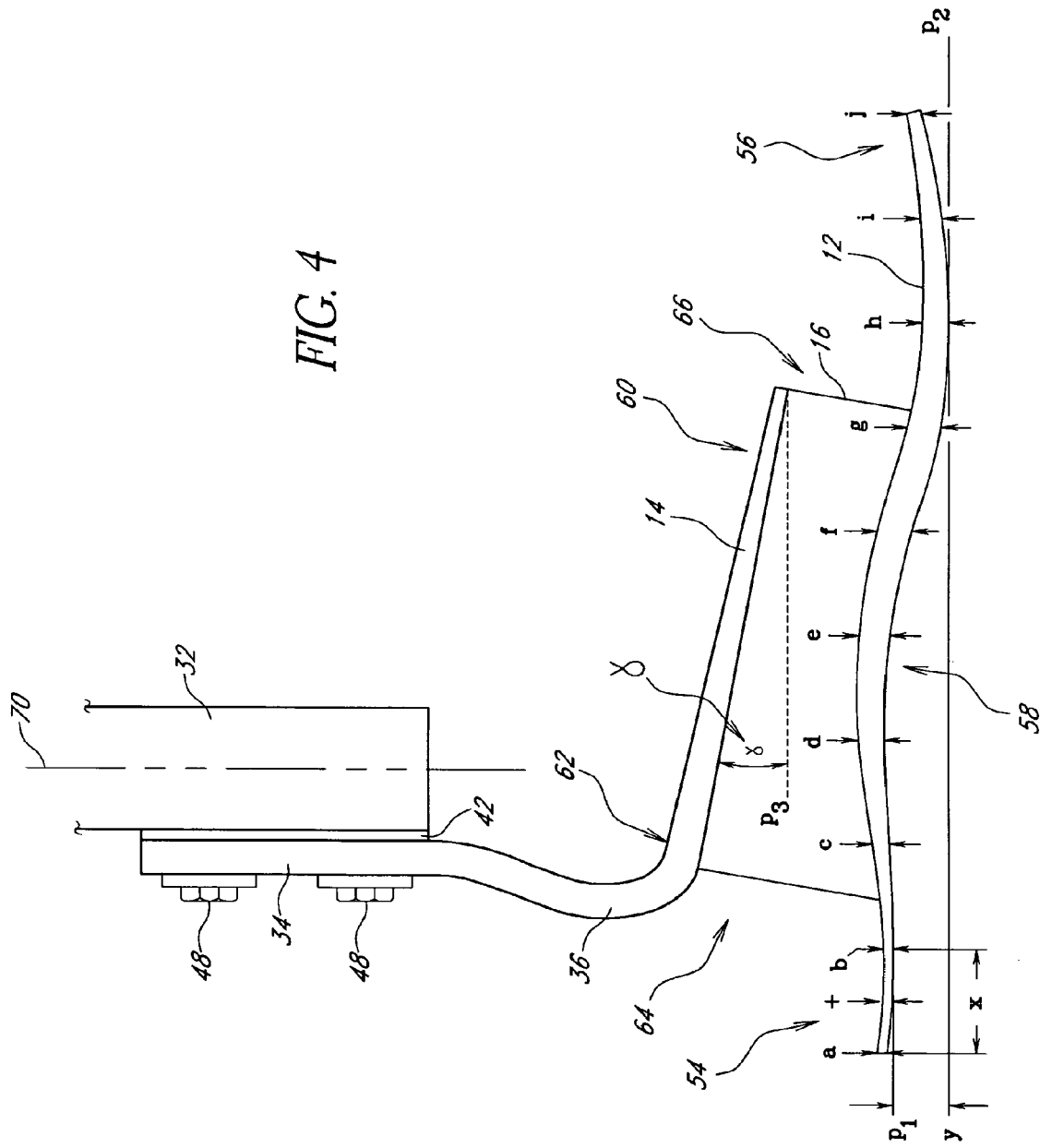
FIG. 4 is a side elevational view of a prosthetic foot more clearly showing a foot plate having a tapered thickness along its length.

As illustrated in FIG. 4, the foot plate 12 is preferably of curvilinear shape. The thickness t of foot plate 12 is preferably tapered along its length, and the tapered profile corresponds approximately to the weight of the amputee. That is, for a heavier amputee, the thicknesses along the length would be greater than for a lighter weight amputee. Generally, the weight groups may be classified as light, medium, or heavy.

Table I below presents preferred groupings, as module sizes C/D/E, of cosmesis sizes corresponding to a male "A" width shoe last. The sizes are presented by length L, width B at the forefoot and width H at the heel of the cosmesis.

TABLE I

Cosmesis Sizes for Male "A" Width Shoe Last

| MODULE | LENGTH L (cm) | WIDTH B (cm) | WIDTH H (cm) |
|---|---|---|---|
| C | 22 | 2.88 | 2.19 |
|   | 23 | 3.00 | 2.25 |
|   | 24 | 3.12 | 2.31 |
| D | 25 | 3.25 | 2.44 |
|   | 26 | 3.38 | 2.50 |
|   | 27 | 3.50 | 2.56 |
| E | 28 | 3.62 | 2.69 |
|   | 29 | 3.75 | 2.75 |
|   | 30 | 3.88 | 2.81 |

Table II below presents preferred module sizes for various weight groups of amputees.

TABLE II

Modules vs. Weight Groups

| | WEIGHT GROUP | | |
|---|---|---|---|
| MODULE | LIGHT | MEDIUM | HEAVY |
| C | CL | CM | — |
| D | DL | DM | DH |
| E | — | EM | EH |

Table III below presents preferred taper thicknesses (t) for an average or "DM" size foot plate 12, taken at positions spaced by distance x=1 inch (2.54 cm).

TABLE III

Taper Thickness t for DM Foot Plate

| POSITION (x = 2.54 cm) | THICKNESS t (cm) |
|---|---|
| a | 0.16 |
| b | 0.16 |
| c | 0.32 |
| d | 0.52 |
| e | 0.69 |
| f | 0.78 |
| g | 0.71 |
| h | 0.60 |
| i | 0.48 |
| j | 0.28 |

The foot plate 12 has a heel end 54, toward the left in FIG. 4, which is concave-upward or slightly uplifted from a horizontal plane P1 tangential to the heel end 54 of the foot plate 12. Similarly, a toe end 56, to the right of FIG. 4, is concave upward or somewhat uplifted from a horizontal plane P2 tangential to the front portion of the foot plate 12. An arch section 58 is formed between the heel and toe ends and is preferably concave-downward, as shown.

It is understood that within the cosmesis 30 (not shown), the tangent plane P1 of the heel end 54 is slightly raised a distance y relative to the tangent plane P2 of the toe end 56, as shown. The DM-sized foot plate of Table III, for example, has y=0.5 inches (1.27 cm). The foot plate 12 is preferably 0.25 inches (0.63 cm) from the bottom or sole of the cosmesis 30. The cosmesis 30 may be insert molded using an anatomically sculpted foot shape, with details and sizing based on a master pattern and/or digitized data representing typical foot sizes.

An intermediate region 58 comprising the arch portion of the foot plate 12 has the greatest thickness of the foot plate 12. The curvature of the arch region 58 is defined by the cosmesis or shoe sole profile, and generally corresponds to selected ranges of human foot lengths.

The foot plate 12 of prosthesis 10 preferably has a length between about 5 and 15 inches (about 13 and 38 cm), more preferably between about 8 and 12 inches (about 20 and 30 cm) for the foot sizes given in Table I. The width of foot plate 12 is preferably about 1 to 4 inches (about 2.5 to 8 cm). For the example given in Table III for a DM-sized foot plate 12, the length of the plate 12 is approximately 9 inches (about 23 cm) and its width is about 2 inches (about 5 cm). The foot plate 12 has a thickness between about 0.05 and 0.4 inches (about 0.1 and 1 cm), which more preferably may be tapered as indicated in Table III.

The ankle plate 14 of prosthesis 10 is substantially planar, and is preferably shorter in length than the foot plate 12 and has a thickness also defined by the weight group of the wearer. The thickness of the ankle plate is preferably about 0.05 to 0.4 inches (0.1 to 1 cm). More preferably, the corresponding ankle plate 14 in the present example is about 0.2 inches (about 0.5 cm) thick at rear portion 62, tapering to a thickness of about 0.1 inches (about 0.25 cm) at front portion 60. The ankle plate 14 preferably has a length of about 3 to 7 inches (about 8 to 18 cm) and a width of about 1 to 3 inches (about 2.5 to 8 cm), more preferably having length-width dimension of approximately 5×2 inches (about 13×5 cm). The ankle plate 14 is positioned at an angle such that its front tip 60 is located closer to the foot plate 12 than its rear tip 68. Relative to plane P3 shown in FIG. 4, the rear tip is preferably raised an angle γ of about 5 to 30 degrees, and more preferably, about 10 degrees.

The ankle block 16 is generally sized such that its upper surface is planar and corresponds to the length and width of the ankle plate 14. The lower surface of the ankle block 16 is substantially curvilinear to mate with the curvilinear surface of foot plate 12. In the present example, the block 16 has a preferred thickness, at its front 66, of about 1 to 3 inches (about 2.5 to 8 cm), more preferably about 1.3 inches (about 3.4 cm). Its thickness tapers to a minimum of about 0.5 to 1 inch (about 1 to 2.54 cm), more preferably about 0.8 inches (about 2 cm) adjacent arch portion 58. The rear 64 of the block 16 is preferably about 1 to 4 inches (about 2.5 to 10 cm) thick, more preferably about 2.6 inches (about 6.6 cm) thick, which is about twice the thickness of the front portion 66 of the block 16. This gives the ankle block a substantially wedge shape. The greater thickness at the rear of block 16 is provided to impart additional support in the rear portion 64 of the ankle block due to greater compressive forces on the rear of the foot prosthesis caused by off-axis application of force relative to axis 70 during heel strike (see FIG. 5A).

The ankle block 16 may be provided in varying heights or thicknesses, as desired, but is most effective with a thickness of between about 1 and 4 inches (about 2.54 and 10 cm). The front portion and rear surfaces of ankle block 16 are preferably angled according to the angle γ defined by the plane P3 and the ankle plate 14. In other words, the ankle block has front and rear surfaces which are preferably sloped forward at an angle γ from vertical. The ankle block thus provides a relatively stiff, yet flexible ankle region which can be customized for various wearers. Heavier wearers may require a denser resilient material for the ankle block, while lighter wearers may require a less dense material or less thickness.

As shown in FIGS. 2 and 3, the spring element 18 is positioned in the ankle block such that the center of the spring element 18, at the position of fastener 26, is located approximately above the arch portion 58 of foot plate 12. The two members 22, 24 of the spring element 18 preferably have a constant thickness of about 0.05 to 0.2 inches (about 0.1 to 0.5 cm). The distance between the two members at front end 82, when no load is impressed onto the foot 10, is preferably about 0.5 and 2 inches (about 1 to 5 cm), more preferably about 0.7 inches (about 1.8 cm). At rear end 80, when no load is impressed on the foot 10, the distance between members 22 and 24 is about 1 to 3 inches (about 2.5 to 7.5 cm), more preferably about 1.4 inches (about 3.5 cm). As described in further detail below, when the foot is in a heel-strike position, the rear end 80 of the spring element is compressed. When the foot is in a toe-off position, the forward end 82 of the spring element is compressed.

The lengths, widths and thicknesses of the foot plate 12, ankle plate 14, ankle block 16 and spring element 18 may be customized for the wearer according to his/her foot size as well as the approximate weight group of the wearer. Likewise, the material choice and size for these elements may be varied according to the wearer's foot size and weight.

The cylindrical openings 50, 51 provided in the fore and aft portions of ankle block 16 preferably have a diameter of about 0.1 to 0.4 inches (about 0.25 to 1 cm), and more preferably, about 0.2 inches (about 0.5 cm). While the openings 50 and 51 shown in FIG. 2 have the same diameter, the diameters of the openings may be different to accommodate different sized stiffeners. For instance, the diameter of opening 51 may be made larger than the diameter of opening 50 to correspond with the greater volume of ankle block 16 in rear portion 64.

Performance Characteristics

Figure 5A:
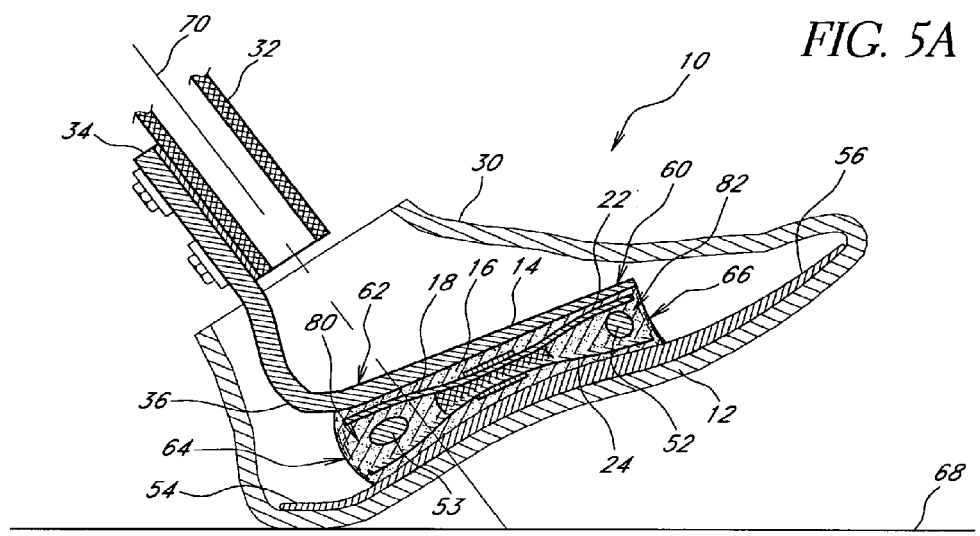
FIG. 5A is a sectional view of a prosthetic foot in a heel-strike position of a walking stride.
Figure 5B:
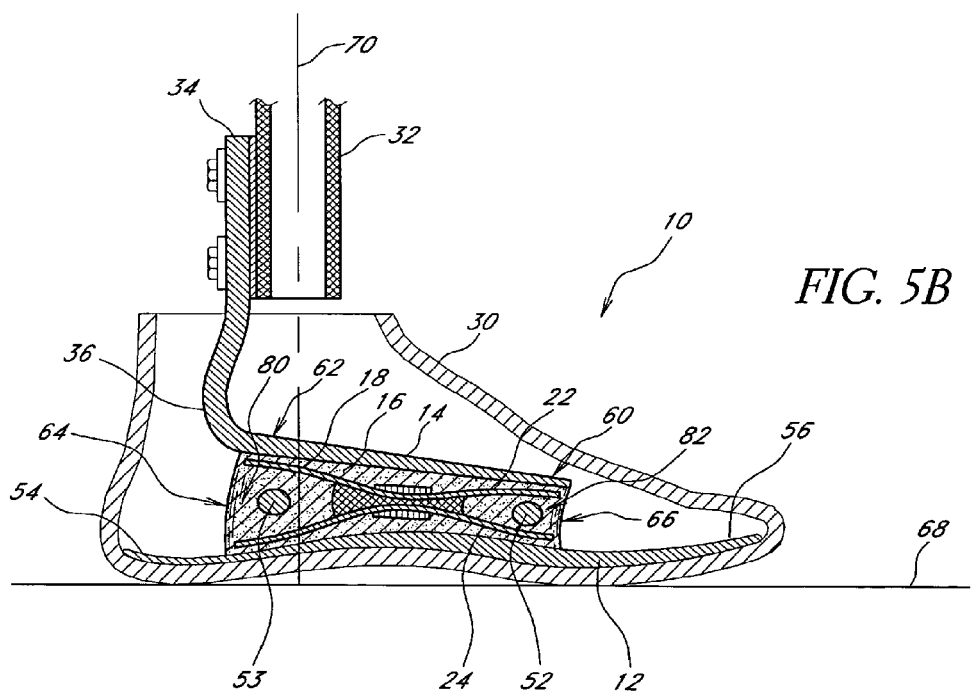
FIG. 5B is a sectional view of a prosthetic foot in a flat position of a walking stride.
Figure 5C:
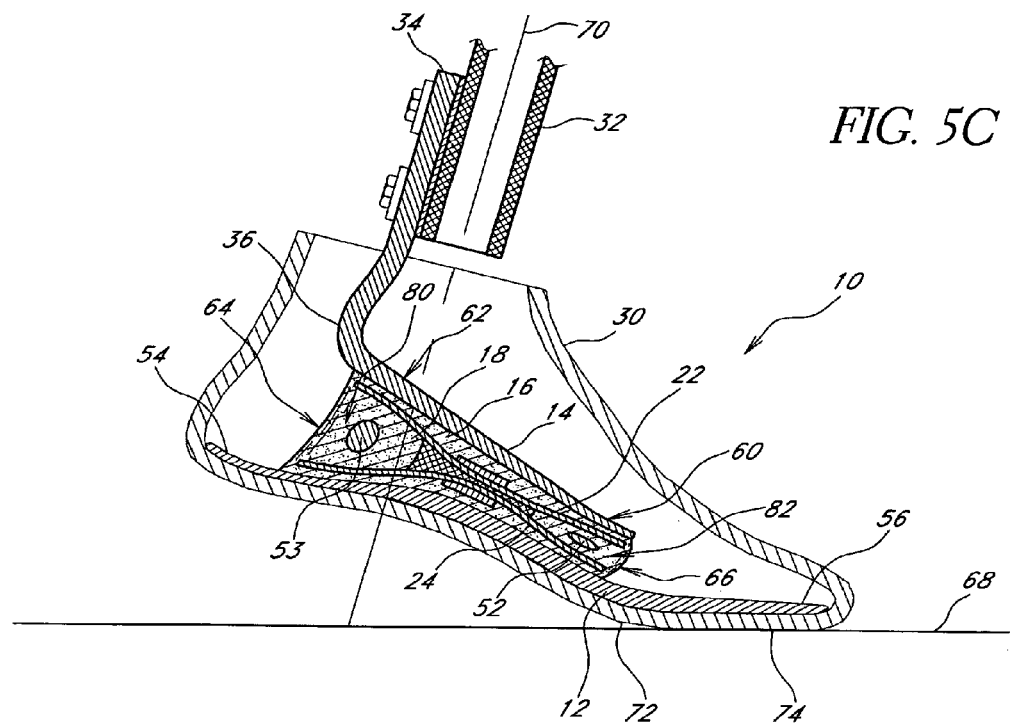
FIG. 5C is a sectional view of a prosthetic foot in a heel-off position of a walking stride.
Figure 5D:
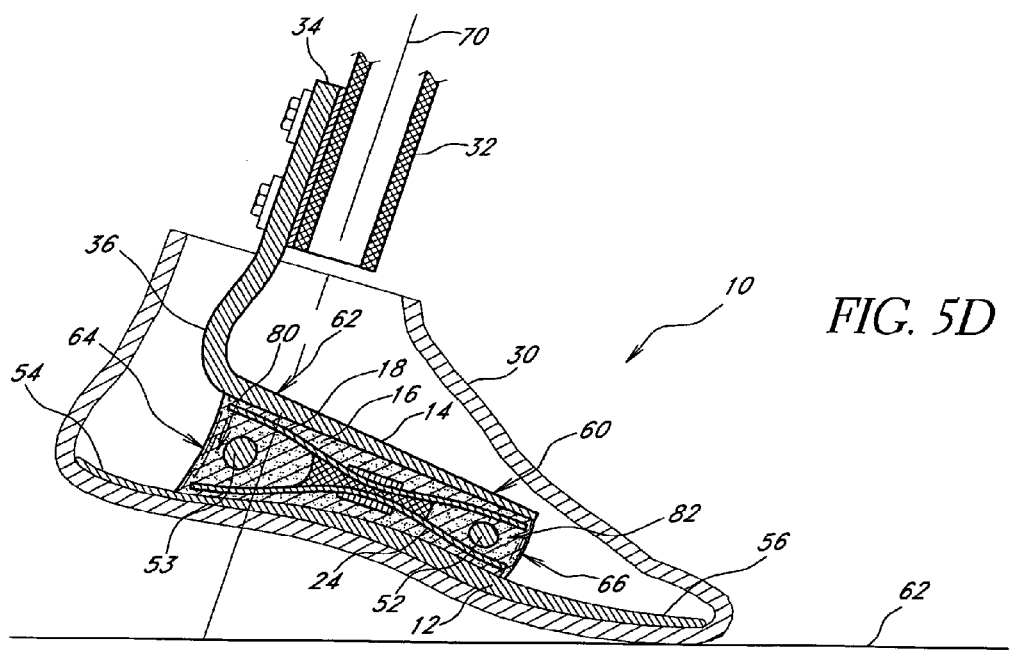
FIG. 5D is a sectional view of a prosthetic foot in a toe-off position of a walking stride.

To more fully explain the improved performance characteristics of the present prosthetic foot 10, FIGS. 5A-5D show "snapshots" of a prosthetic foot in several positions of a walking stride. More particularly, FIG. 5A shows a heel-strike position, FIG. 5B shows a generally flat or mid-stance position, FIG. 5C shows a heel-off position, and FIG. 5D shows a toe-off position. Throughout the various positions shown for a walking stride, the present prosthetic foot 10 provides a smooth and generally life-like response to the wearer. During a walking stride, the ankle block 16 transmits the forces imparted thereon by the foot plate 12 and ankle plate 14, and experiences a gradual rollover, or migration of the compressed region, from rear to front.

With specific reference to FIG. 5A, a first position of a walking stride generally entails a heel strike, wherein the wearer transfers all of his or her weight to the heel of the leading foot. In this case, a rear portion 54 of the foot plate 12 comes in contact with a ground surface 68, albeit through the cosmesis 30. The flexible nature of the foot plate 12 allows it to bend slightly in the rear portion 54, but most of the compressive stresses from the weight of the wearer through the prosthetic foot 10 to the foot plate 12 are absorbed by a rear region 64 of the ankle block 16 with spring element 18. The spring element 18 in the rear portion contracts, such that the distance between members 22 and 24 at rear end 80 decreases. In a front region 66 of the ankle block 16, the spring element 18 may expand slightly such that the distance between members 22 and 24 at front end 82 increases. Front portion 66 of the ankle block 16 experiences a stretching, or tension, due to the attachment along the entire lower edge of the ankle block with the foot plate 12, while rear portion 64 experiences compression. The contraction of the spring element 18 at end 80 and ankle block 16 at end 64 allows the prosthesis 10 to absorb and store energy from the compressive stresses during heel strike. Further, a slight amount of bending may occur in a rear region 68 of the ankle plate 14. The rear stiffener 53 between members 22 and 24 is compressed so as to provide necessary support to the foot prosthesis and to prevent separation of the members 22, 24 from the wedge 28. Front stiffener 52 is slightly stretched substantially vertically due to the tension forces at front portion 66 of ankle block 16.

Next, in FIG. 5B, the wearer reaches a generally flat-footed or mid-stance position, whereby the foot plate 12 contacts the ground 68 along substantially its entire length, again through the cosmesis 30. In this position the weight of the wearer is directed substantially downwardly, so that the compression along the length of the ankle block 16 is only slightly greater in the rear portion 64 than in front portion 66, due to the off-center application of force. In both the fore and rear ends of spring element 18, the members 22 and 24 are compressed towards each other, with the rear end 80 being slightly more compressed from its original position than the forward end 82. Likewise, stiffeners 52 and 53 are compressed due to the downward application of force. Although this view freezes the compressive stress distribution as such, in reality the weight of the wearer is continually shifting from behind the centerline 70 of the attachment member 34 to forward thereof. Thus, as the wearer continues through the stride, the compression of the ankle block 16 and the elements embedded within travels from the rear portion 64 toward the front portion 66. This migration of the compressed region can be termed "rollover".

In a next snapshot of the walking stride, FIG. 5C shows the prosthetic foot 10 in a "heel-off" position. This is the instant when the wearer is pushing off using ball 72 and toe 74 regions of the foot. Thus, a large compressive force is generated in the front region 66 of the ankle block 16, causing the rear region 64 to experience a large amount of separation or tension. Similarly, the spring element 18 at the rear end 80 expands between the two members 22, 24, while it compresses in the front end 82. The front tip 56 of the foot plate 12 may bend substantially to absorb some of the compressive stresses. Likewise, the front tip 60 of the ankle plate 14 may bend somewhat at this point. It is important to note that although the ankle block 16 absorbs a majority of the compression generated by the wearer, the foot plate 12 and ankle plate 14 are designed to work in conjunction with the resilient ankle block and spring element and provide enhanced dynamic performance. Further, the flexing of the foot plate 12 and ankle plate 14 relieves some of the extreme shear stresses applied to the interfaces between the ankle block 16 and plates, thus increasing the life of the bonds formed therebetween. The stiffener 52 located in the front 66 of the ankle block 16 compresses so as to limit compression of front end 82, giving the wearer balance and to prevent separation of the members 22, 24 from the wedge 28. Stiffener 53 extends due to the separation of ankle block 16 in rear portion 64.

In FIG. 5D, a final position of the walking stride is shown, wherein the prosthetic foot 10 remains in contact with the ground 68, but some of the weight of the wearer is being transferred to the opposite foot, which has now moved forward. In this "toe-off" position, there is less bending of the front tip 56 of the foot plate 12 and less compression of the front portion 66 of the ankle block 16 and front end 82 of spring element 18. Likewise, the front tip 60 of the ankle plate 14 may flex a slight amount, depending on the material and thickness utilized. The region of highest compression of the ankle block 16 remains at the farthest forward region 66, but it is reduced from the compression level of the heel-off position of FIG. 5C. Thus, the rear portion 64 of the ankle block 16 experiences a small amount of tension or spreading.

It can now be appreciated that the "feel" of the present prosthetic foot is greatly enhanced by the cooperation between the foot plate, ankle plate, ankle block and spring inserts. As the wearer continues through the walking stride the dynamic response from the prosthetic foot is smooth as the ankle block with spring inserts compresses in different regions. Further, the flexing of the ankle and foot plates assist in smoothly transmitting the various bumps and jars found in uneven walking surfaces.

Alternative Embodiments

It will be appreciated that many alternative embodiments of a prosthetic foot having features and advantages in accordance with the present invention may also be constructed and used with efficacy. One such alternative embodiment is shown in FIG. 6. Reference numerals for FIG. 6 generally correspond to the reference numerals used in FIGS. 1-5D for like elements. Thus, the prosthetic foot 10 shown in FIG. 6 generally comprises a lower foot plate 12, an upper, smaller ankle plate 14, an ankle layer or block 16 made of resilient material, connecting the foot plate 12 to the ankle plate 14, and a spring element 18 embedded within the ankle block. The foot plate 12 has a length and width roughly equal to the approximate length and width of the particular wearer's amputated foot and sized to fit within an outer, flexible cosmesis 30, shown in phantom. As shown in FIG. 6, the ankle plate 14 has a substantially arcuate curvature extending from the integrally formed attachment member 34 to the front of the ankle plate 14.

More particularly, the spring element 18 as illustrated in FIG. 6 is a resilient support member inserted within the resilient ankle block 16. The spring element 18 shown in FIG. 6 is preferably a plate-like member with a curvilinear concave downward shape and a substantially rectangular vertical projection. The spring element 18 is preferably made from a carbon fiber composite material such as described hereinbefore, although other similar materials may be used as well.

FIG. 7 illustrates another alternative embodiment of the invention. Again, like reference numerals are generally used to indicate like elements. Thus, the prosthetic foot 10 shown in FIG. 7 generally comprises a lower foot plate 12, an upper, smaller ankle plate 14, and an ankle layer or block 16 made of resilient material, such as solid or foam rubber or polyurethane, and connecting the foot plate 12 to the ankle plate 14. The foot plate 12 has a length and width roughly equal to the approximate length and width of the particular wearer's amputated foot and sized to fit within an outer, flexible cosmesis 30, shown in phantom. As shown in FIG. 7, the ankle plate 14 transitions into a substantially arcuate or curved ankle section 36 which is preferably integrally formed between the attachment member 34 and the ankle plate 14.

FIG. 8 illustrates yet another alternative embodiment of the invention. Again, like reference numerals are generally used to indicate like elements. Thus, the prosthetic foot 10 shown in FIG. 8 generally comprises a lower foot plate 12, an upper, smaller ankle plate 14, and one or more ankle blocks 16a, 16b made of resilient material, such as solid or foam rubber or polyurethane, and connecting the foot plate 12 to the ankle plate 14. If desired, the posterior ankle block 16a may have a density or compliance characteristic which is different than that of the anterior ankle block 16b, so as to render it more soft and more compliant, for example, than the anterior ankle block 16b. For instance, this configuration could provide a more compliant heel response during heel strike.

Ankle blocks 16a, 16b may be formed integrally or separately, as desired or as expedient. Preferably, they are positioned closely adjacent to one another so as to occupy substantially the entire space between the foot plate 12 and the ankle plate 14. The foot plate 12 preferably has a length and width roughly equal to the approximate length and width of the particular wearer's amputated foot and sized to fit within an outer, flexible cosmesis 30, shown in phantom. As shown in FIG. 8, the ankle plate 14 transitions into a substantially arcuate or curved ankle section 36 which is preferably integrally formed between the attachment member 34 and the ankle plate 14.

Figure 9:
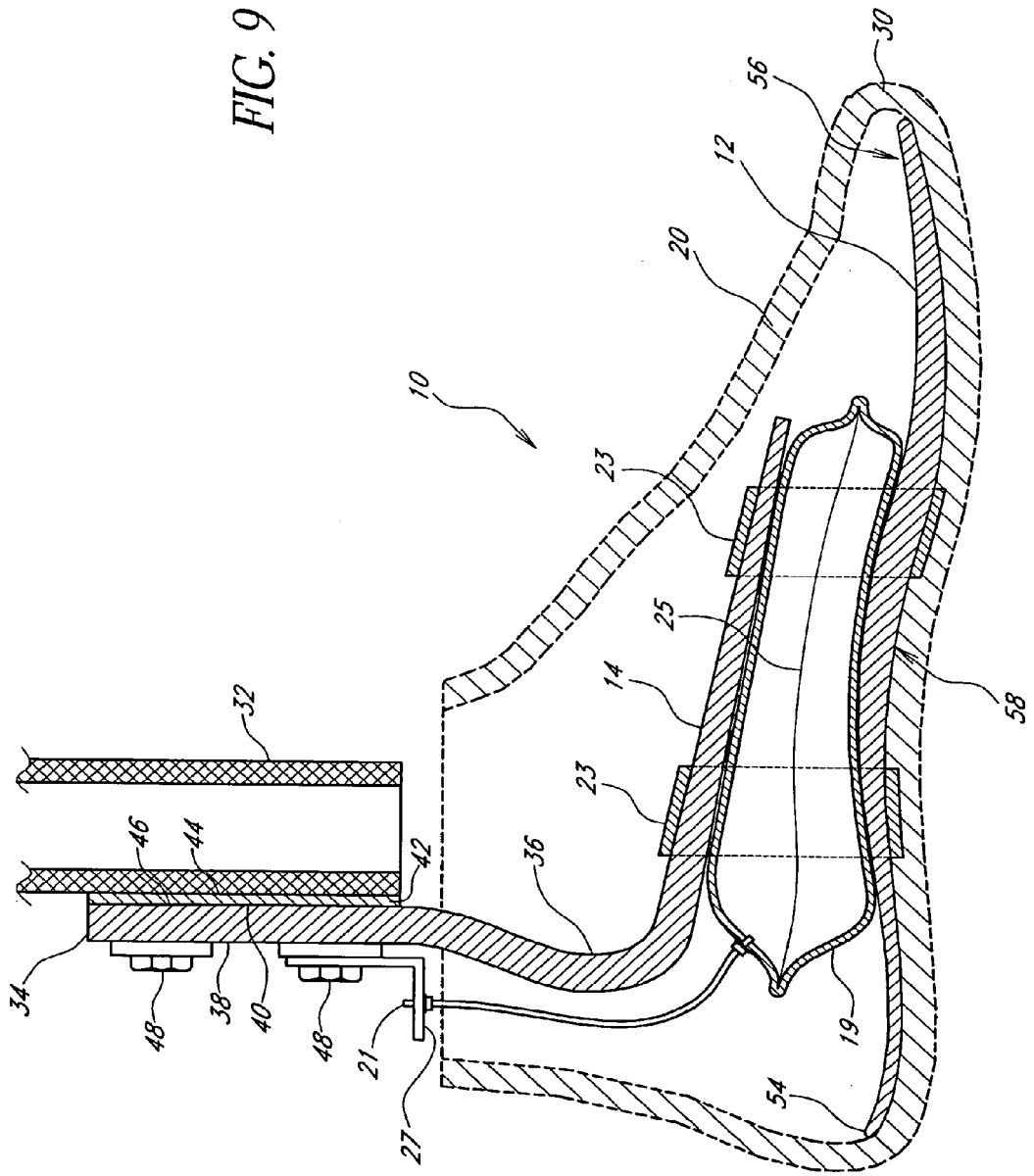
FIG. 9 is a cross-sectional view of another alternative embodiment of a prosthetic foot of the present invention incorporating an inflatable bladder ankle block.
Figure 10:
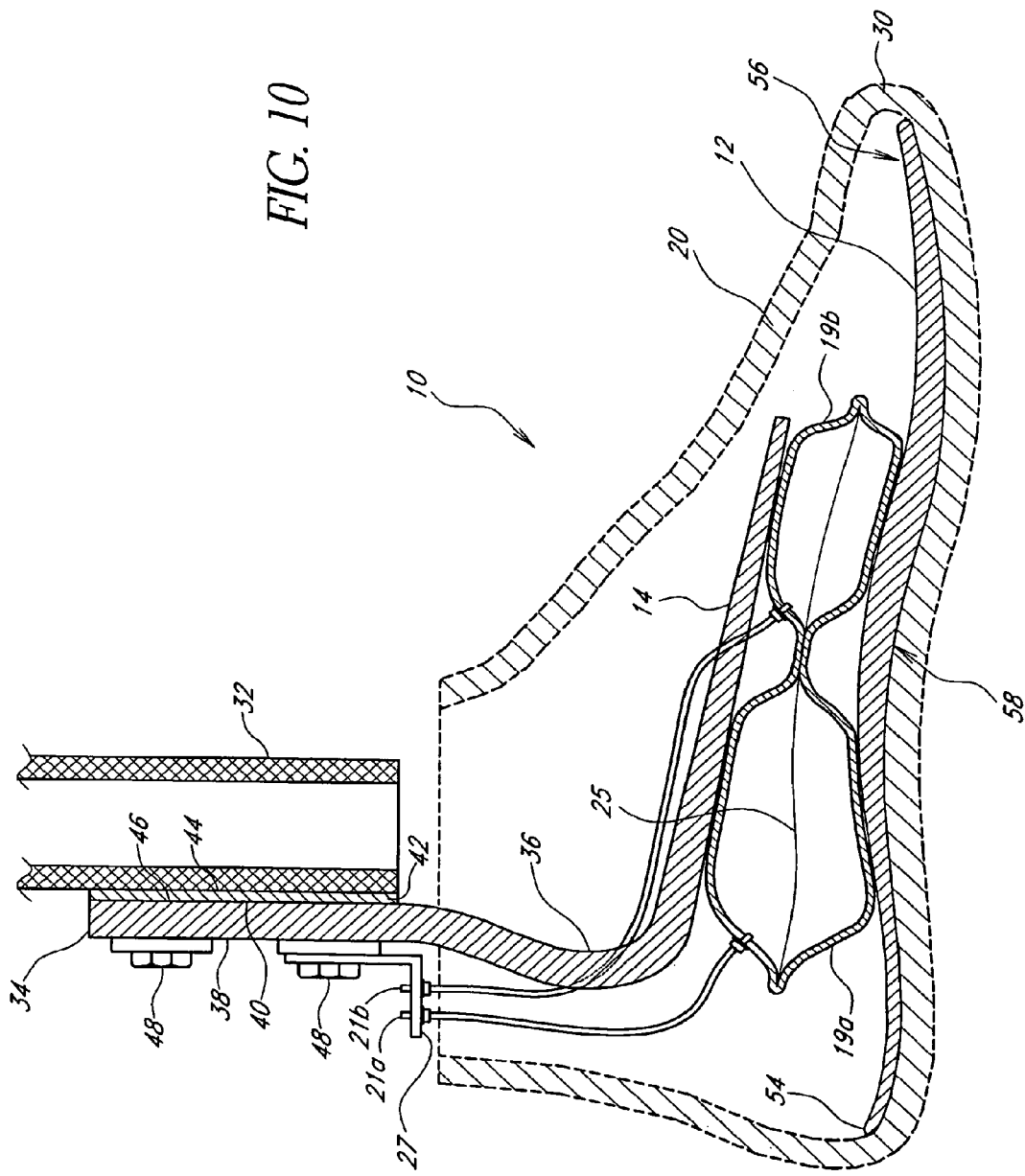
FIG. 10 is a cross-sectional view of another alternative embodiment of a prosthetic foot of the present invention incorporating a multiple inflatable bladder ankle block.

FIGS. 9 and 10 illustrate two other possible alternative embodiments of the invention. Again, like reference numerals are generally used to indicate like elements. Thus, the prosthetic foot 10 shown in FIG. 9 generally comprises a lower foot plate 12, an upper, smaller ankle plate 14, and, in this case, an inflatable bladder 19 disposed between the foot plate 12 and the ankle plate 14. The bladder 19 has the further advantage in that it enables the patient or prosthetist to vary the performance characteristics of the prosthesis by adjusting the pressure in the bladder 19. This may be accomplished, for example, through the provision of a valve means 21, which is provided in communication with the bladder 19. In a preferred embodiment, the valve 21 is adapted to receive a needle from an air pump (not shown) or from a $CO_2$ cartridge (described with respect to FIG. 16B below), and may be suitably disposed on bracket 27, as illustrated in FIGS. 9 and 10. The valve 21 may be operatively connected to bladder 19 via tubing or other suitable communication passage.

The bladder 19 may be secured via adhesive or other suitable affixing means to the upper ankle plate 14 and the lower foot plate 12 so as to provide substantially the sole means of connection and support therebetween. Optionally, one or more retaining straps 23 may be used to provide primary or secondary connection support, as needed or desired. Strap 23 may be fabricated from any number of suitably tough, flexible materials such as epoxy-impregnated canvas or the like. For example, straps 23 may be operatively attached to the forefoot portion of the prosthetic foot 10 as illustrated in FIG. 9 via adhesive, or nuts and bolts, or may be releasably attached around the structural member 12, 14 through the provision of Velcro□-type fasteners or similar expedient.

The straps 23 provide a number of benefits. For example, if juxtaposed to a bladder member 19, the strap may be appropriately tightened to 'flatten' the bladder, thus increasing the contact area between the structural members 12, 14 and the bladder. Moreover, restraining means such as the straps 23 may be incorporated to restrict the distance that the associated structural members 12, 14 may move from one another. The straps 23 may also be utilized to prevent undesirable excessive loading and stressing of the structural members 12, 14 and/or the bladder 19.

The bladder 19 is preferably fabricated from a suitably strong, flexible, leak-proof, lightweight material such as urethane or the like. By way of example, the bladder may be formed by heat sealing appropriately sized and shaped pieces of urethane sheet to each other. Suitable thicknesses of urethane sheet material have been found to be 0.01 to 0.02 inches (0.25-0.50 mm), but a wide range of suitable thicknesses and materials may also be utilized with efficacy. Bladder pressures of up to 80 psi (5.5 bar) have been utilized with efficacy.

The bladder 19 is preferably enwrapped in a covering material of Kevlar or similarly strong material to prevent the bladder 19 from exploding under high pressures and to help define the final inflated shape of the bladder. In preferred embodiments, a covering may include top and bottom sections which are stitched together at the perimeter 25 of the bladder 19. Those skilled in the art will understand that a variety of covering materials and methods of fabrication and assembly thereof may be also utilized with efficacy, without departing from the teachings of the invention.

Bladder 19 may enclose air, CO2, or a similar gas-like substance, or may alternatively enclose liquids or gels such as water, silicone, or the like. Any such assembly is preferably selected and adjusted to provide the desired deformability and consequent 'cushioning' effect or energy-storing, absorption and release.

The bladder 19 may comprise a single chamber bladder, as illustrated in FIG. 9, or, optionally, it may comprise a multiple chamber bladders with or without venting provided between adjacent chambers. For example, the bladder could be bifurcated into anterior and posterior chambers or portions 19a, 19b such that the posterior portion 19a can be adjusted to have a compliance characteristic which is different than that of the anterior portion 19b, so as to render it more soft and more compliant, for example, than the anterior portion. This may be desirable, for instance, to provide a more compliant heel response during heel strike. If desired or expedient, the bladder 19 may be tapered in shape so as to permit operative and proper alignment of the bladder between the ankle plate 14 and the foot plate 12.

Optionally, a spring element identical or similar to that illustrated and described above in connection with FIGS. 2-5, may be provided substantially completely within the bladder 19 (FIG. 9) so as to provide primary or supplemental support between the foot and ankle plates, as desired. For, example, the spring element may comprise two relatively flat carbon fiber composite members secured at their middle and separated at their ends. This gives the spring element a preferable shape of a bow tie or double wishbone. During walking, the combination of the resilient spring element and inflatable bladder provides a smooth and adjustable rollover characteristic from a heel-strike to a toe-off, as desired.

The foot plate 12 preferably has a length and width roughly equal to the approximate length and width of the particular wearer's amputated foot and sized to fit within an outer, flexible cosmesis 30, shown in phantom. As shown in FIGS. 9 and 10, the ankle plate 14 transitions into a substantially arcuate or curved ankle section 36 which is preferably integrally formed between the attachment member 34 and the ankle plate 14.

Figure 11B:
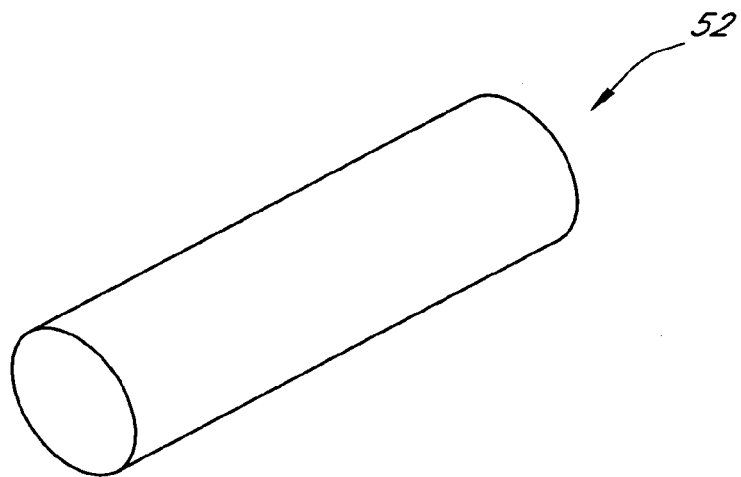
FIGS. 11B-11D are perspective views of stiffeners that may be inserted into the cavities of the prosthetic foot of FIG. 11A.

FIG. 11A illustrates another prosthetic foot 10 similar to that described in FIGS. 1-4 above, but with several modifications as described below. Accordingly, the prosthetic foot 10 of FIG. 11A generally comprises a lower foot plate 12, an upper, smaller ankle plate 14, an ankle layer or block 16 made of resilient material, connecting the foot plate 12 to the ankle plate 14, and cylindrical slots or cavities 50 and 51 allowing for the insertion of optional stiffeners 52 and 53 (see FIGS. 11B-11D). The foot plate 12 has a length and width roughly equal to the approximate length and width of the particular wearer's amputated foot and sized to fit within an outer, flexible cosmesis 30, shown in phantom. As shown in FIG. 11A, the ankle plate 14 has a substantially arcuate curvature extending from the integrally formed attachment member 34 to the front of the ankle plate 14.

The ankle block 16 of FIG. 11A preferably has a front surface that is sloped from the front edge of the ankle plate 14 forward to the foot plate 12 there below. Similarly, the rear surface of the ankle block 16 is preferably also sloped in a forward direction from the rear of the ankle plate 14 in a forward direction to the foot plate 12. A strap 23 such as described above is provided around the ankle plate 14, ankle block 16 and foot plate 12, preferably over a rear portion of the prosthetic foot.

Figure 11C:
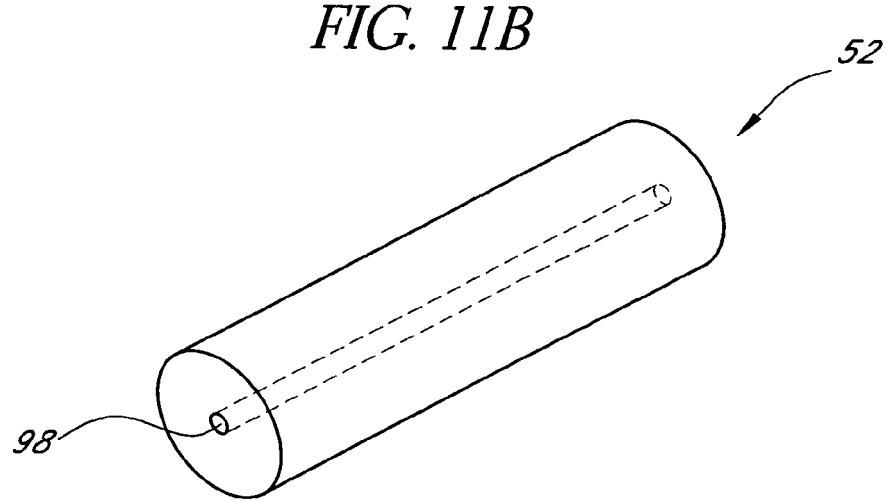
Figure 11D:
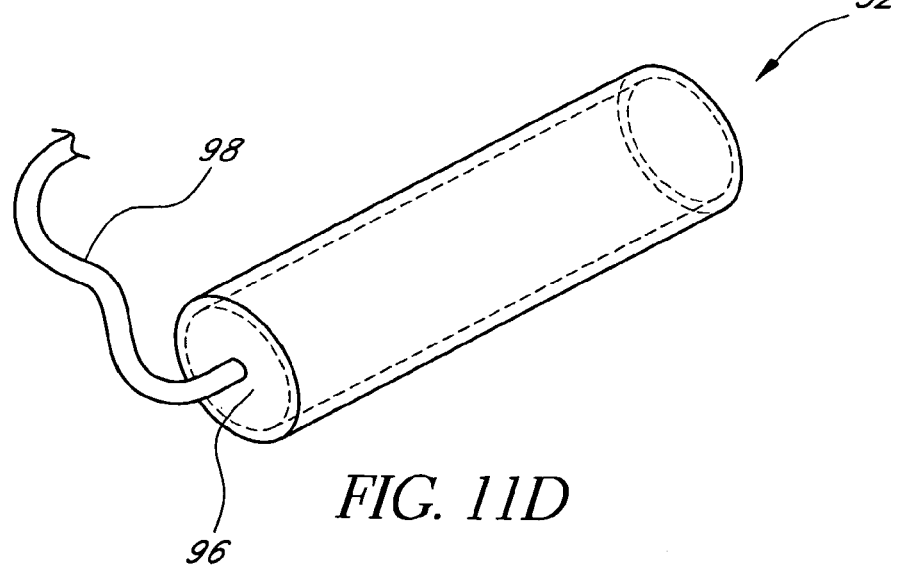

FIGS. 11B-11D show three examples of stiffeners that can be inserted into the cavities 50 or 51. FIG. 11B illustrates a stiffener 52 (or 53) that is substantially cylindrical in shape and is comprised substantially entirely out of foam. FIG. 11C shows a similar cylindrical stiffener 52, having a cylindrical opening 96 extending therethrough and open on each end such that the stiffener is hollow and has a substantially tubular configuration. The size of the opening 96 can be varied to achieve a desired degree of compliance for the stiffener 52. FIG. 11D illustrates a stiffener 52 defining a cylindrical cavity 96 therein being closed at each ends. A tube 98 is connected to the cavity 96 such that air or another gas or fluid can flow into and out of the opening to provide a desired pressure within the opening to control the degree of compliance of the stiffener. Thus, the opening 96 serves as an inflatable bladder. One or more valves (not shown) may be connected to the tube 98 to regulate the flow of air into and out of the bladder 96.

FIG. 12 illustrates another embodiment of a prosthetic foot 10 similar to that shown in FIG. 11A, except that in FIG. 12 there are provided two ankle plates 14 and 15 layered on top of one another in sliding arrangement. The top plate 14 is preferably monolithically formed from a high strength composite material with a curvilinear ankle section 36 and an upper attachment area 34, such as described above. The bottom plate 15 is also preferably monolithically formed with a curvilinear ankle section 37 and an upper attachment area 35. The upper attachment areas 34 and 35 are preferably attached to pylon member 32 through coupling device 42, with bolts or screws (not shown) extending through the upper attachment areas 34 and 35 and coupling device 42 into the pylon member 32.

The lower plate 15 preferably extends forward past the front of ankle plate 14, and more preferably the plate 15 extends to the front of the ankle block 16. Strap 23a secures the plates 14 and 15, the ankle block 16 and the foot plate 12 at the rear of the ankle block. Strap 23b secures the plates 14 and 15 at the front of the plate 14. By providing an upper and lower plate 14 and 15, respectively, these plates are capable of bending and sliding relative to each other. This advantageously reduces the bending resistance of the prosthesis while maintaining adequate vertical support strength.

FIGS. 13 and 14 illustrate another alternative embodiment for a prosthetic foot 10 similar to the embodiment shown in FIG. 10 above. Thus, the foot 10 generally comprises a lower foot plate 12, an upper, smaller ankle plate 14, and a plurality of inflatable bladders disposed between the foot plate 12 and the ankle plate 14. More preferably, a rear or heel bladder 19a is provided near the rear of the ankle plate 14, and a pair of toe bladders 19b which are in fluid communication with each other are provided at the front of the ankle plate (see FIG. 14). A strap 23 is provided at the rear of the ankle plate 14 surrounding the bladder 19a and foot plate 12. Optionally, plates 29a, 29b, 29c and 29d may be provided between each of the bladders and the ankle plate 14 and/or foot plate 12.

The pressure in the heel bladder 19a is controlled by valve 21a, while pressure in the toe bladders 19b is controlled by valve 21b. It will be appreciated that although FIG. 13 shows one valve 21b controlling the pressure in both toe bladders 19b, it is also contemplated that each toe bladder 19b may be controlled by separate valves. The valves 21a and 21b may be operatively connected to the bladder via tubing or other suitable communication passages. In the embodiment shown in FIG. 13, tubings 17a and 17b connect the heel bladder 19a and toe bladders 19b, respectively, to the appropriate valves. Beyond the valves 21a and 21b, the tubings 17a and 17b are preferably joined, with a single tubing 17c extending away therefrom to a gas or air input/output source 21d. A valve 21c controls the pressure through the tubing 17c.

It will be appreciated that the valve control system described with respect to FIGS. 13 and 14 may be used with other types of inflatable bladders. For instance, valves such as FIGS. 13 and 14 may be used to inflate a stiffener 52 such as illustrated in FIG. 11D above. Furthermore, separate tubings may be used to adjust pressure in multiple stiffeners provided in an ankle block as described with respect to FIG. 11A.

Figure 15A:
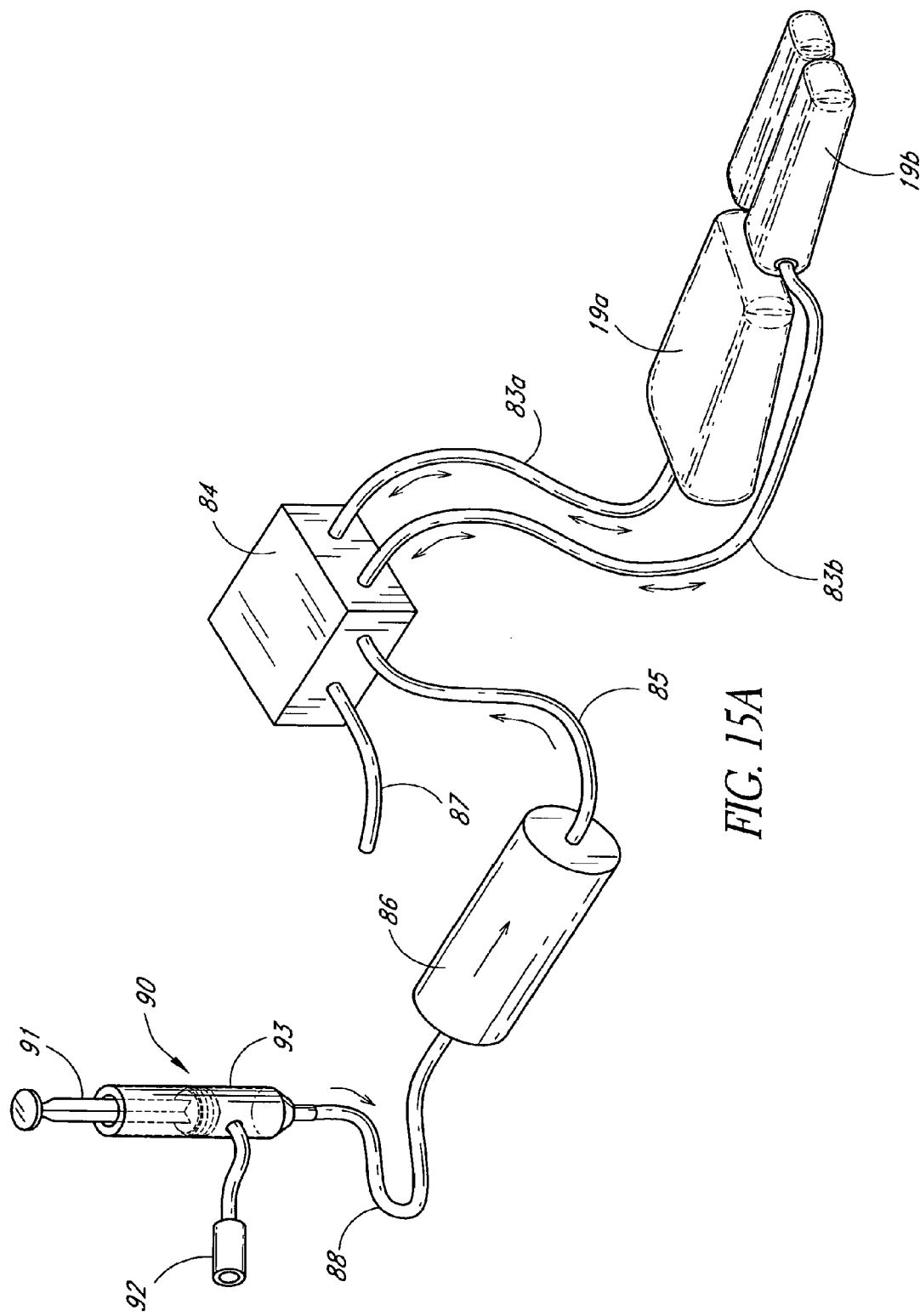
FIG. 15A is a perspective view of the components of another alternative embodiment of a prosthetic foot of the present invention incorporating a shock pumping system.

FIGS. 15A-16A illustrate another embodiment of a prosthetic foot 10 incorporating an air pump system for actively or passively controlling pressure within inflatable bladders. The components of this system are shown in FIG. 15A. A syringe type air pump 90 is provided with an air intake port 92 having a check valve. The syringe pump 90 is connected by a tube 88 to an accumulator 86. The accumulator 86 is connected by a tube 85 to an electronic control system 84 including a valve manifold. Also connected to the control system 84 are an air vent 87, and tubes 83a and 83b providing fluid communication to inflatable bladders 19a and 19b, respectively.

Figure 16A:
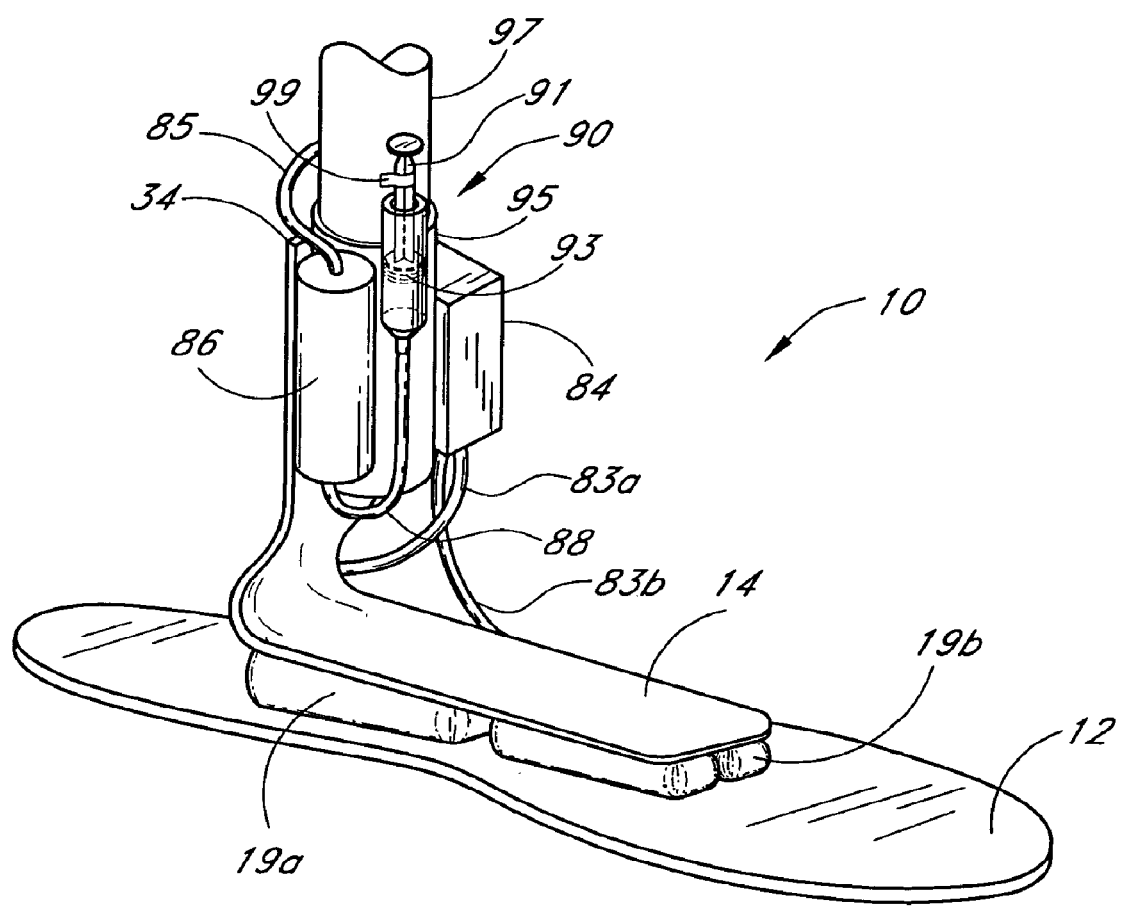
FIG. 16A is a perspective view of another alternative embodiment of a prosthetic foot of the present invention incorporating the components of FIG. 15A.

These components are collectively arranged into a prosthetic foot 10, shown in FIG. 16A. It will be appreciated that the arrangement of components in FIG. 16A is purely exemplifying and thus other arrangements are possible as well. As described in other embodiments above, the inflatable bladders 19a and 19b are provided between ankle plate 14 and foot plate 12. Connected to the upper attachment area 34 of the prosthetic foot 10 are a pair of schematically shown telescoping pylons 95 and 97. Further details regarding telescoping and other types of pylons that may be used in conjunction with the embodiments of the present invention are described below and in applicant's copending application entitled SHOCK MODULE PROSTHESIS, Ser. No. 09/289,533, filed Apr. 19, 1999, and U.S. Pat. No. 5,458,656, the entirety of each of which are hereby incorporated by reference. Lower pylon 95 telescopically engages upper pylon 97, such that pylons 95 and 97 are preferably slidingly and rotationally interengaged with each other. Preferably, a resilient element, such as a coil compression spring, is proximally fixed within upper pylon 97 and distally fixed within lower pylon 95. Thus, when a force is applied to the prosthetic foot, the pylons 95 and 97 move toward one another in a compressed configuration. When the force is released, the pylons move apart to a rest configuration.

The syringe 90 preferably includes a plunger 91 and a cylinder 93. Plunger 91 is attached to the upper pylon 95, such as with bracket 99 or other means. Cylinder 93 is preferably similarly attached to the lower pylon 97. Control system 84 and accumulator 86 are also preferably attached to lower pylon 97. Accordingly, when force is applied to the prosthetic foot 10, the relative movement of the pylons causes the plunger 91 to move in and out of the cylinder 93 and produce air pressure through the tube 88. Air is preferably drawn through a filter element comprising air intake port 92 (not shown in FIG. 16A). The fluid is stored in accumulator 86 and passed on to the valve manifold of the electronic control system 84. The manifold preferably electronically controls how much air is provided to each of the inflatable bladders 19a and 19b, and also how much air will be vented out through tube 87. Thus, the pump system of FIGS. 15A-16 uses pressure built up by the amputee's own motion and determines an appropriate pressure to be provided to each of the inflatable bladders.

Figure 15B:
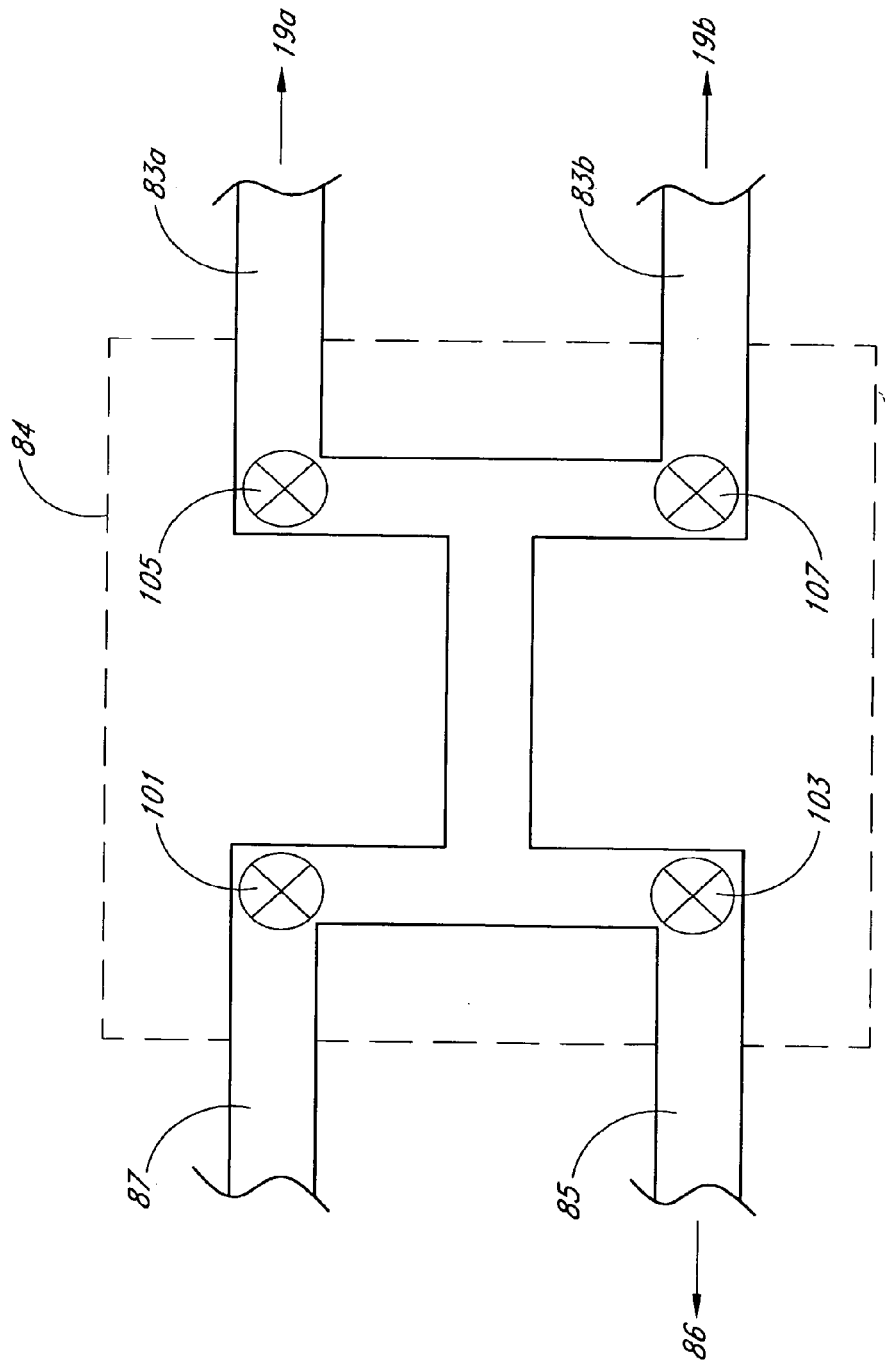
FIG. 15B is a schematic view of the valve manifold of the prosthetic foot of FIG. 15A.

For example, FIG. 15B illustrates schematically one embodiment for the valve manifold of the control system 84. When the bladders 19a and 19b require more air for additional support, the control system 84 opens valves 103, 105 and 107 to allow air to pass from the accumulator 86 to the bladders 19a and 19b through tubes 83a and 83b. When it is desired to deflate bladders 19a and 19b, the valve 101 can be opened and valve 103 can be closed so that air passes from the bladders 19a, 19b through tubes 83a and 83b and out tube 87. In addition, when one of the bladders requires more or less air than the other, valves 105 and 107 can be selectively adjusted to individually inflate or deflate bladder 19a or 19b, with either valve 101 or valve 103 remaining open. The valves can be sensed and controlled electronically or via a computer. It will be appreciated that a variety of valve configurations may be employed to selectively adjust the appropriate pressure for the bladders 19a and 19b.

It will further be appreciated that although FIG. 16A depicts the syringe as being attached externally to the pylons, the syringe may also be attached internally to the pylons. Furthermore, other components of the pump system, such as the accumulator and the valve manifold, may also be provided within the pylons. One such embodiment is described by FIG. 23, below.

Figure 16B:
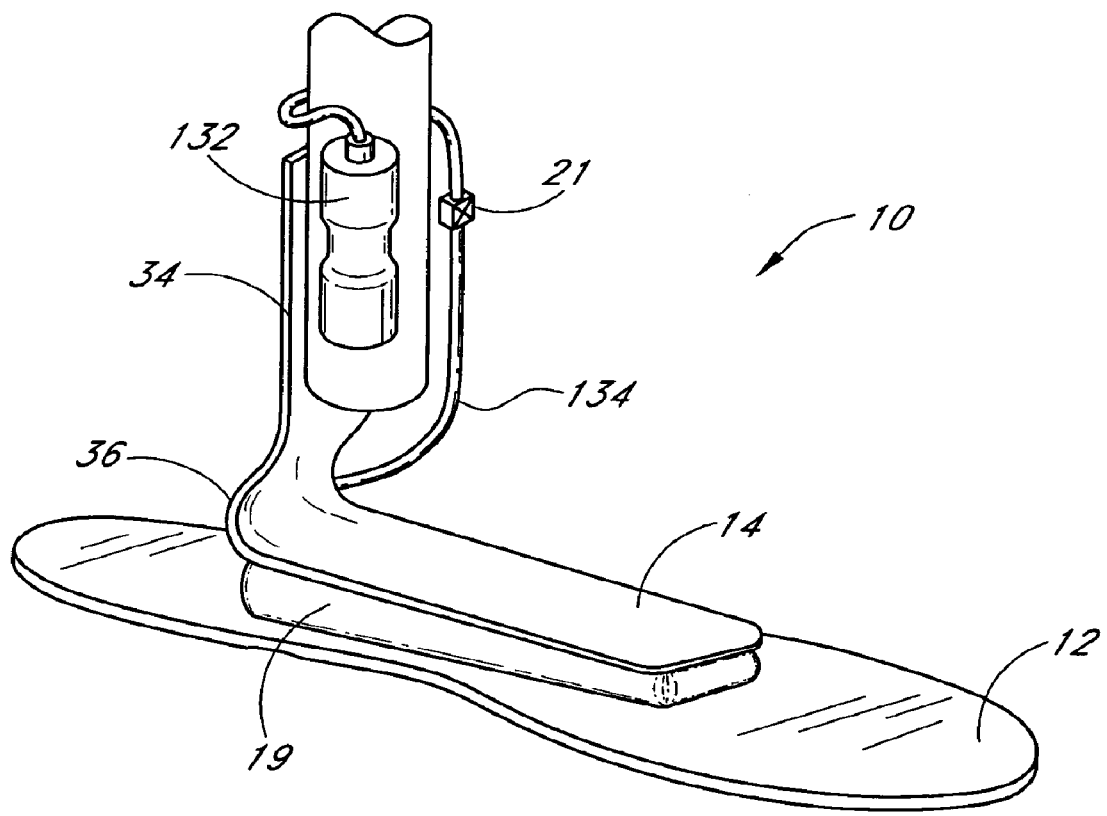
FIG. 16B is a perspective view of one embodiment of a prosthetic foot incorporating a $CO_2$ cartridge.

FIG. 16B illustrates another prosthetic foot incorporating an inflatable bladder 19 and a CO2 cartridge for adjusting the pressure within the bladder. The embodiment of FIG. 16B is similar to the prosthetic foot of FIG. 9, and includes an inflatable bladder 19 sandwiched between an upper ankle plate 14 and a lower foot plate 12. A pylon 32 is attached to the ankle plate 14 through a vertically oriented upper attachment member 34 and a curvilinear ankle section 36, all of which are preferably monolithically formed. A $CO_2$ cartridge 132 is preferably attached to the exterior surface of the pylon 32, and is connected to the bladder 19 through a fluid line 134 having a valve 21. The valve 21 in one embodiment is electrically controlled, with a pressure sensor to control the amount of CO2 delivered to the bladder.

FIG. 17 shows another embodiment of a prosthetic foot 10. This embodiment is similar to that shown in FIG. 12 above in that it generally comprises two ankle plates 14 and 15, an ankle block 16 and a foot plate 12. However, in the prosthetic foot 10 of FIG. 17, the plates 14 and 15 both extend to the front of the ankle block 16. Furthermore, the ankle plate 16 is more preferably a chambered urethane having a plurality of openings extending therethrough. Specifically, in addition to the cylindrical slots 50 and 51, the ankle block 16 of FIG. 17 also has an opening 55 that is substantially oblong when viewed from the side and that extends across the transverse dimension of the ankle block 16. Similar to the embodiments described above, the opening 55 can be filled with other materials for adjusting the stiffness of the block. Openings can be enclosed, if desired, defining closed chambers filled with a compressible fluid such as air.

FIG. 18 shows a similar embodiment to that of FIG. 17, except that the ankle block 16, in addition to the cylindrical slots 50 and 51, has three additional openings 55a, 55b and 55c. More preferably, slots 55a and 55c are cylindrical similar to slots 50 and 51, while slot 55b has a substantially dual concave-out shape when viewed from the side. All five of these openings can remain empty or may be filled with stiffeners and/or fluid as described above. It will be appreciated that the number and shapes of these openings may be varied giving due consideration to the goals of the desired prosthetic foot. None, some or all of the openings filled may be filled with stiffeners, in order to obtain desired performance characteristics for the foot 10.

FIG. 19 illustrates another embodiment of a prosthetic foot 10. Like the embodiments described above, this foot includes two ankle plates 14 and 15, an ankle block 16 and a foot plate 12. The ankle block 16 also includes cylindrical slots 50 and 51 similar to those described above. Within the slots 50 and 51 are inserted cams 112 and 114 that rotate about shafts 113 and 115, respectively. These rotatable cams, when inserted, cause the shape of the slots to deform elliptically in compliance with the shape of the cams. This in turn adjusts the compliance of the ankle block depending on the orientation of each of the cams. Thus, as shown in FIG. 19, one cam may be oriented such that its cross-section is aligned substantially transversely relative to a forward walking motion, while the other cam may be oriented such that its cross-section is aligned substantially parallel to a forward walking motion. These cams may be rotated while within the ankle block 16 to different orientations as well.

The cams are preferably made from a material stiffer than that of the ankle block 16, and more preferably, made be made of metal or other materials. Thus, inserting a cam into the ankle block 16 increases the stiffness of that part of the ankle block. Moreover, as shown in FIG. 19, when one cam 112 is oriented substantially transversely to a forward walking motion, and another cam 114 is oriented substantially parallel to a forward walking motion, the transverse cam 112 preferably imparts greater stiffness to that part of the ankle block than does the other cam 114. Furthermore, because the cams are rotatable, the stiffness in each portion of the ankle block is adjustable. It will also be appreciated that although FIG. 19 shows only two cams, fewer or greater number of rotatable cams can also be incorporated into the ankle block.

FIG. 19 also illustrates a strap 110 attached to the rear face of upper attachment area 35 of ankle plate 15. This strap 110 preferably extends down and is attached to the foot plate 12. The strap 110 advantageously is provided to adjust the relative flexing properties between the ankle plates and the foot plate and to control the maximum distance between the respective plates. It will be appreciated that the strap shown in FIG. 19 may be incorporated in any of the embodiments above in which an ankle support member is provided between an ankle plate and a foot plate.

Figure 20:
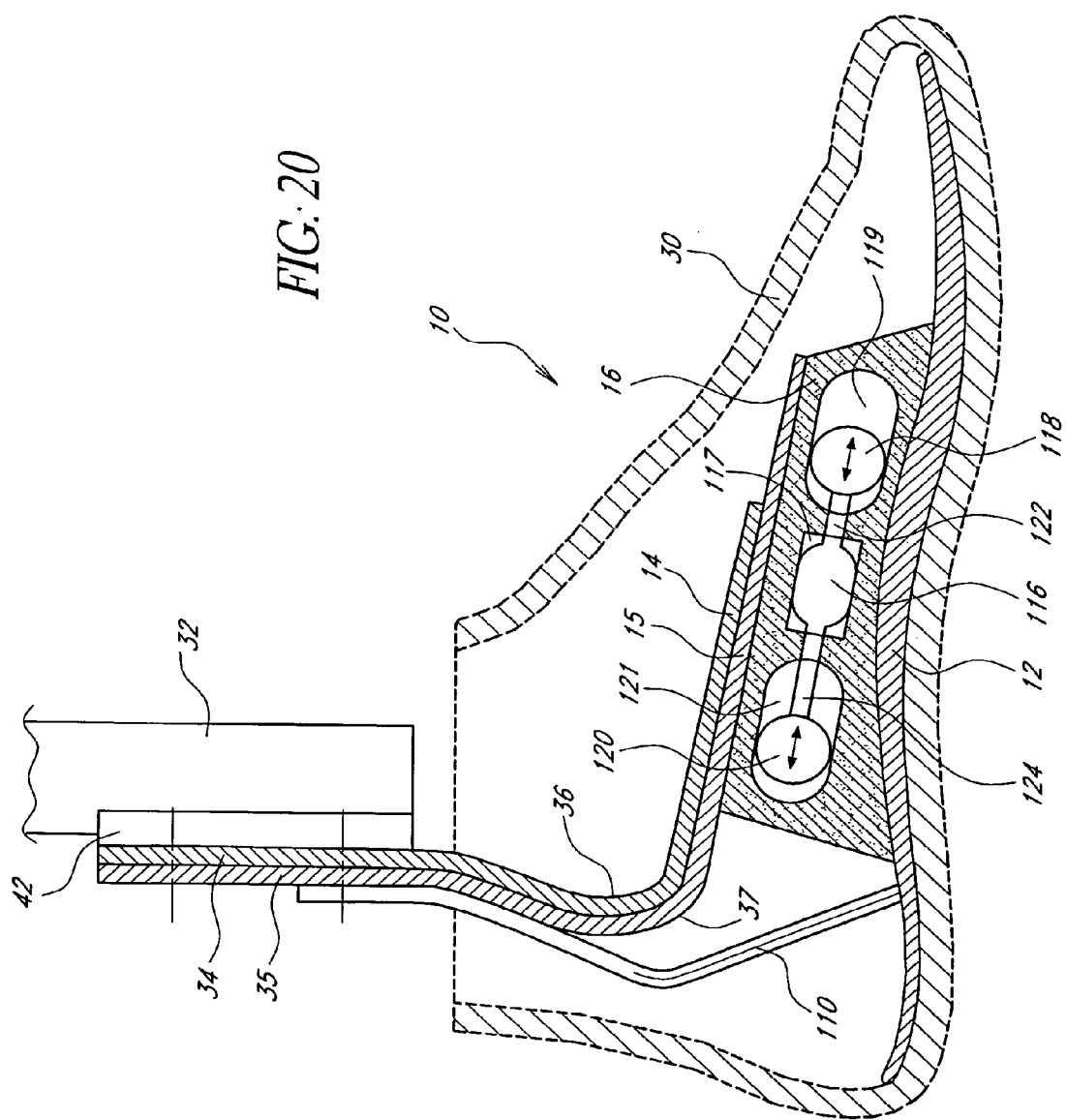
FIG. 20 is a partial cross-sectional view of another alternative embodiment of a prosthetic foot of the present invention incorporating an actuator and moveable stiffeners.

FIG. 20 illustrates another embodiment of a prosthetic foot 10. In this embodiment, the ankle block 16 includes a front chamber 119 and a rear chamber 121, each containing a stiffener 118 and 120, respectively, arranged transversely therein relative to a forward walking motion. The chambers 119 and 121 are sized to allow the stiffeners 118 and 120 to move forward and backward relative to a forward walking motion within each of the chambers. Thus, as shown in FIG. 20, when the stiffeners are generally circular when viewed from the side, each of the chambers has an oblong shape. By being able to move the stiffeners 118 and 120 within the ankle block 16, a user can selectively adjust the stiffness of the prosthetic foot by changing the position of the stiffeners.

In the embodiment shown in FIG. 20, the stiffeners 118 and 120 are cylindrical rods which are attached to arms 122 and 124, respectively. These arms are joined in a middle chamber 117 by an actuator 116, schematically shown in FIG. 20. In one embodiment, the actuator 116 is a motor that preferably adjusts the location of the stiffeners 118, 120 in the chambers 119, 121 to provide desired stiffness in a particular location of the ankle block 16. The motor 116 may, for example, be a manual or servo motor. In one embodiment, the arms 122 and 124 are integrally formed such that a constant distance is maintained between the front stiffener 118 and the rear stiffener 120. The motor 116 then adjusts the position of the arms such that the stiffeners are in the same relative position within each of their respective chambers.

It will be appreciated that other embodiments are also possible. For instance, the stiffeners need not be separated by a constant distance, and can be adjustable to shorten or lengthen the distance therebetween. This may be accomplished, for example, by providing the actuator 116 as a knob that can be turned in one direction to shorten the distance between the stiffeners and in the other direction to lengthen the distance between the stiffeners. In such an embodiment, the arms 122 and 124 may be opposingly threadingly engaged with the actuator 116. Furthermore, it will be appreciated that where the actuator 116 is a knob, the stiffeners can be separated by a constant distance with integrally formed arms 122 and 124, with the knob capable of being turned to adjust the location of the stiffeners within their respective chambers while maintaining a constant distance therebetween.

Figure 21:
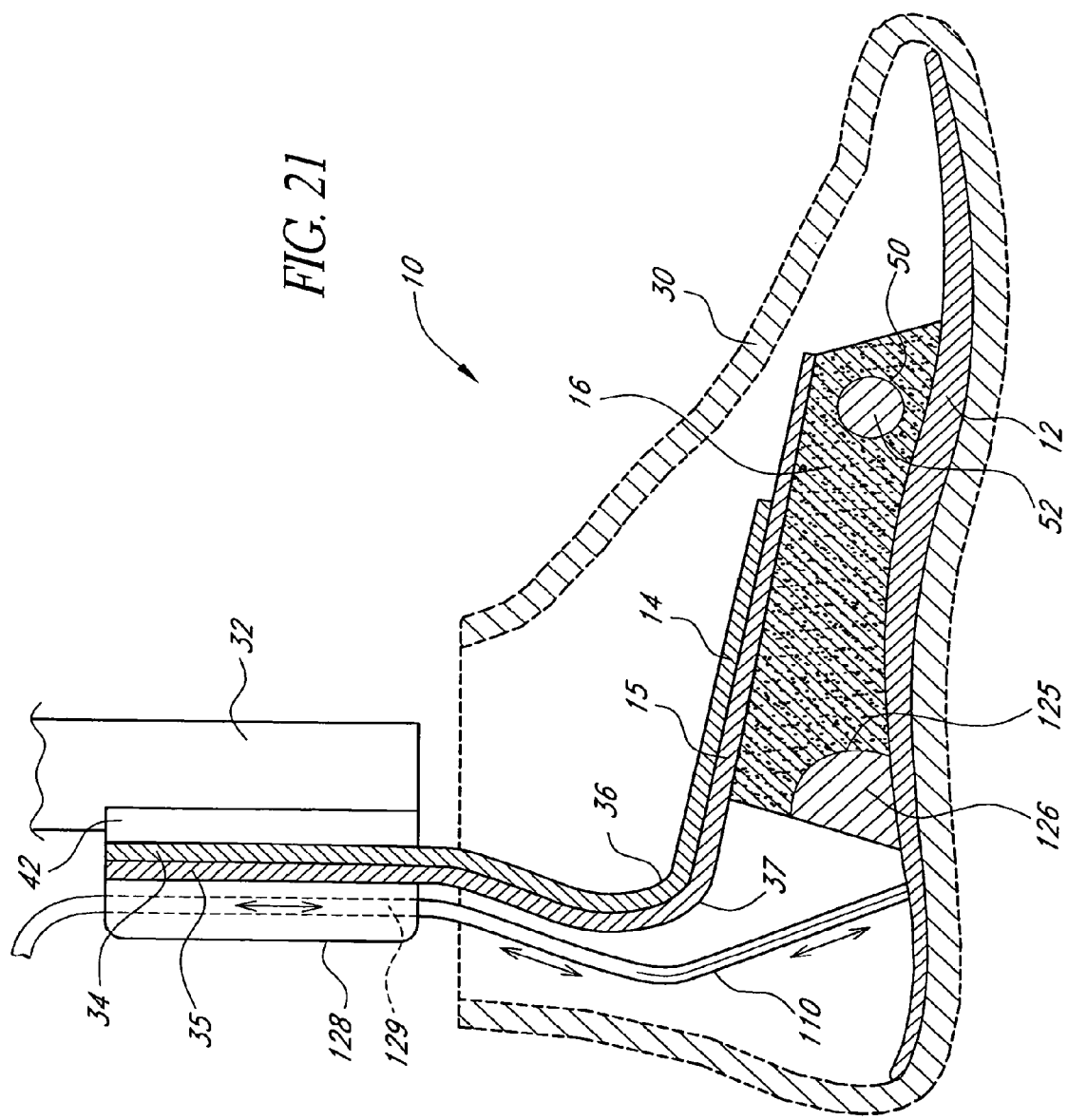
FIG. 21 is a partial cross-sectional view of another alternative embodiment of a prosthetic foot of the present invention incorporating an adjustable strap and an insertable heel wedge piece.

FIG. 21 illustrates another embodiment of a prosthetic foot 10. Similar to the embodiments above, this prosthetic foot 10 includes an ankle block 16 disposed between ankle plates 14 and 15 and foot plate 12. The ankle block 16 preferably includes a single cylindrical slot 50 in the fore portion of the block, the slot 50 including a stiffener 52 therein. It will be appreciated, however, that additional slots may be provided in the ankle block 16 as described above.

As shown in FIG. 21, the ankle block 16 preferably includes in the rear portion a wedge cut-out 125 adjacent to and extending to the foot plate 12. The cut-out 125 is preferably disposed directly below the pylon 32 to correspond substantially to the location of a human heel. More preferably, a wedge piece 126 is inserted into the cut-out 125 of the ankle block 16 to provide additional support in the heel portion of the prosthetic foot 10. In one embodiment, as shown in FIG. 21, the wedge piece 126 has a rear surface that is substantially flush with the rear surface of the ankle block and has a convex shape that mates with the wedge cut-out 125. The wedge piece is preferably fabricated from urethane rubber, although other materials may be used as well. Because the wedge piece 126 is removable from the ankle block 16, wedge pieces of varying stiffness may be inserted into the wedge cut-out to provide desired degrees of stiffness in the heel. For example, a wedge piece that has a stiffness that is greater or less than that of the ankle block may be inserted into the wedge cut-out. It will also be appreciated that using wedge pieces of different sizes and shapes may also provide desired compliance characteristics. Thus, the prosthesis may be used without a wedge piece 126, or with a wedge piece of varying size or stiffness to adjust the performance characteristics of the prosthesis.

Figure 22:
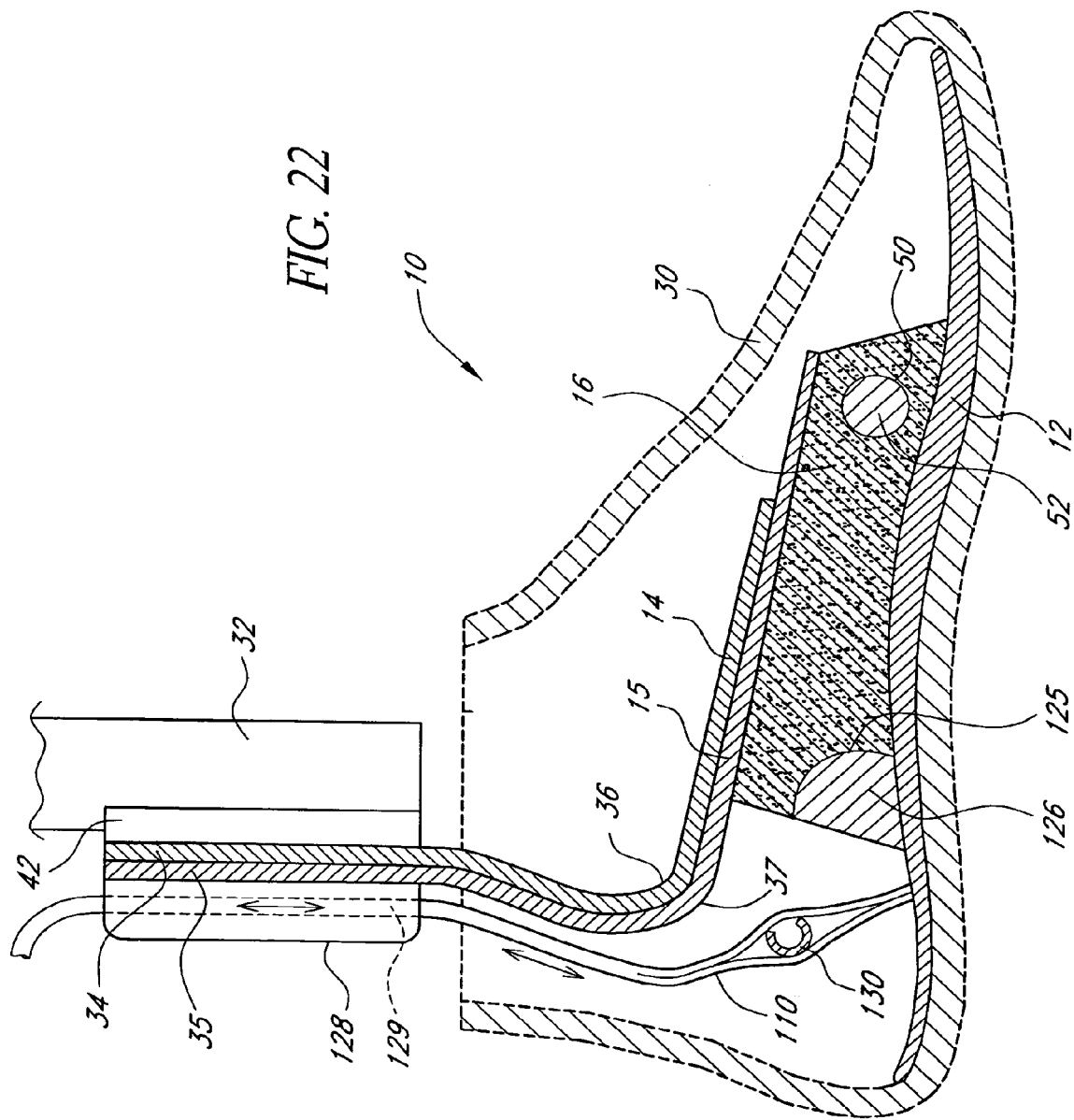
FIG. 22 is a partial cross-sectional view of the prosthetic foot of FIG. 21, further illustrating a C-shaped insert for tightening the adjustable strap.

FIG. 21 also illustrates a strap 110 incorporated with an adjustment mechanism connected to the pylon 32. A housing 128 for the strap is provided on the rear surface of the upper attachment area 35, the housing having a slot 129 extending vertically therethrough. The strap 110 is preferably able to move through the slot 129 in order to tighten or loosen the connection with the foot plate 12, as indicated by the arrows shown in the figure. Within the slot 129 the strap can be held and locked in place by any appropriate means, such as a press-fit, screws, pins, brackets, etc. FIG. 22 further illustrates that an insert, such as a C-shaped insert 130, can be placed within adjacent and connecting portions of the strap 110 to further adjust the tension in the strap.

Figure 23:
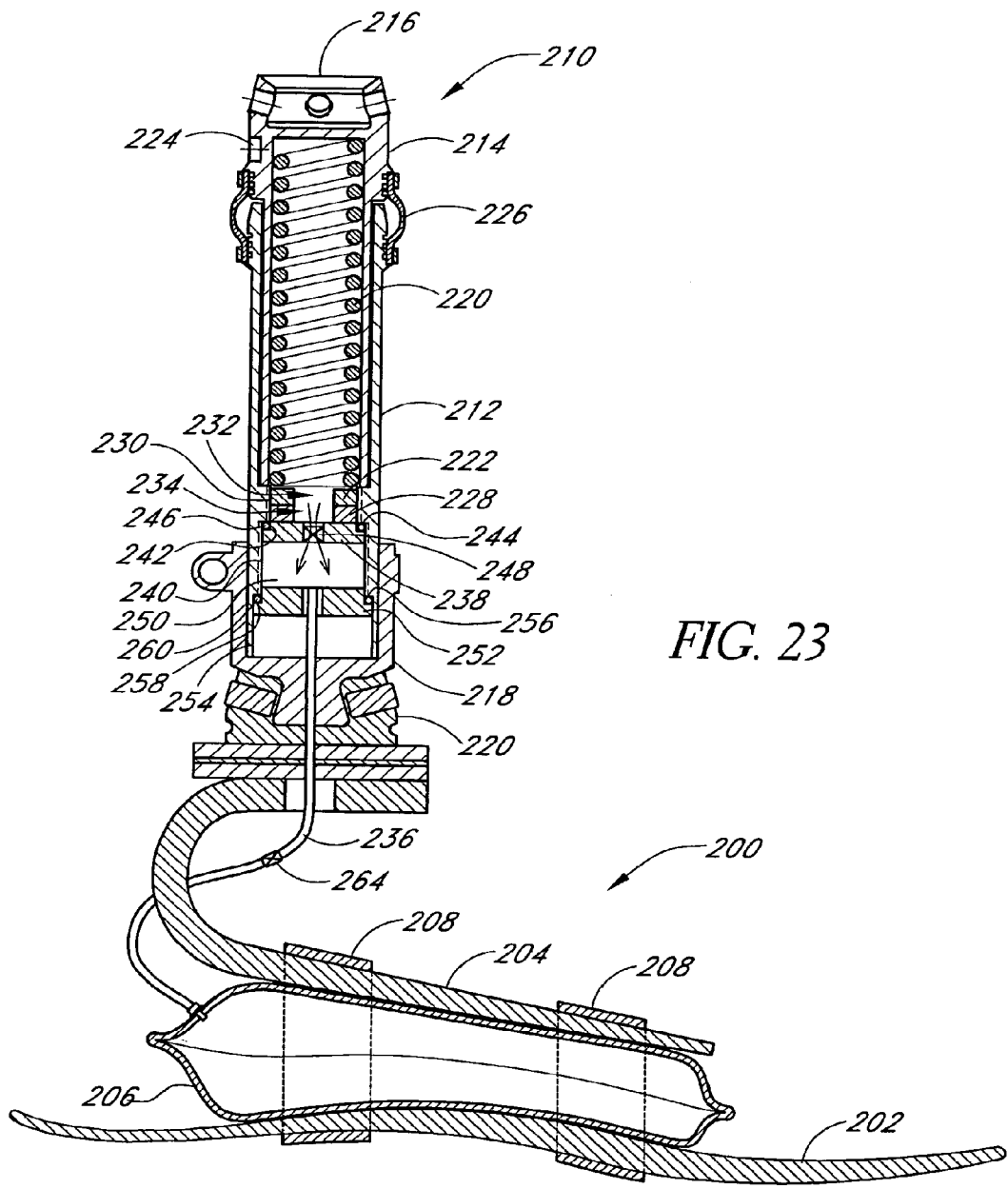
FIG. 23 is a partial cross-sectional view of prosthetic foot having an inflatable bladder in fluid communication with an active shock module.

In another embodiment, a syringe-type air pump system similar to that shown in FIGS. 15A-16 is produced by the action of the telescoping pylons as shown in FIG. 23. In such an embodiment, an inner pylon 214 acts as the plunger of the syringe, and an outer pylon 212 acts as the cylinder of the syringe. As the inner pylon 214 is compressed and decompressed toward and away from the outer pylon 212 with a spring 220 or other compression member, fluid pressure is generated within a chamber defined between the two pylons. When the inner pylon 214 is the upper of the two pylons, the inner pylon is preferably sealed at the top of the chamber, and the outer pylon is preferably sealed at the bottom of the chamber. More preferably, the sealing of the chamber may be provided using valves 224, 248 to regulate fluid flow into and out of the chamber. A valve 248 provided at the bottom of the chamber in the outer pylon preferably leads to a fluid reservoir 250, which may be provided within the outer pylon or separately therefrom. As with the accumulator above, the reservoir 250 may be connected via a fluid line 236 to an inflatable bladder 206 that supports a prosthetic foot.

More particularly, FIG. 23 illustrates a prosthetic foot 200 having an inflatable bladder similar to that shown in FIG. 9. Similar to the prosthetic foot described above, the prosthetic foot 200 generally comprises a lower foot plate 202, an upper, smaller ankle plate 204, and an inflatable bladder 206 disposed between the foot plate 212 and the ankle plate 214. The bladder 206 is preferably secured to the plates through straps 208, or by other means as described above.

The pressure in the bladder 206 is controlled through connection to an active shock module 210. Shock module 210 includes outer pylon 212 and inner pylon 214, shaped and adapted for smooth relative motion. Pylons 212 and 214 are preferably slidingly and rotationally interengaged with each other while retaining their operative horizontal alignment with each other through a relatively close fit between the inside dimensions of outer pylon 212 and the outside dimensions of inner pylon 214. The inner pylon 214 has an enlarged outside diameter at its proximal end, approximately equal to the outside diameter of the outer pylon 212. This enlarged diameter portion of the inner pylon 214 therefore extends beyond the proximal end of the outer pylon 212 and does not extend into the outer pylon 212.

Pylon 214 also has a female pyramid fitting 216 at its proximal end, for attachment to a stump socket (not shown). Outer pylon 212 preferably has a cylindrical outer surface to facilitate the attachment of various types of prosthetic feet using conventional prosthetic couplers. For example, the lower end of pylon 212 may be attached to prosthetic foot 200 via a pyramid coupler 218 and female pyramid fitting 220. The female coupler 218 is slipped over the lower extremity of the outer pylon 212 and clamped into position.

Shock module 210 preferably includes a hybrid spring-fluid resilient element, comprising an internal coil compression spring 220 in combination with a compressible fluid such as air. Spring 220 is preferably proximally fixed with respect to inner pylon 214 and distally fixed with respect to outer pylon 212 via spring support 222. Optionally, a valve 224 is provided within pylon 214 to vary the pressure of the fluid inside of shock module 210. A torque-resisting cuff 226 provides torsion-resistance to the prosthesis and also keeps dirt and other debris from getting between pylons 212 and 214 and affecting their relative motion. Further details on shock modules that may be used in conjunction with the embodiments of the present invention may be found in U.S. application Ser. No. 09/556,249, entitled ACTIVE SHOCK MODULE PROSTHESIS, filed Apr. 24, 2000, the entirety of which is hereby incorporated by reference.

An end cap 228 is preferably provided below the spring support 222 within the outer pylon 212. Both the end cap 228 and the spring support 222 are preferably threaded to engage an internally threaded surface 230 of the outer pylon 212. Both the spring support 222 and the end cap 228 preferably have an internal hole 232, 234, respectively, which allows the compressible fluid to pass therethrough to a fluid reservoir 250, described below. A cover cap 238 preferably seals the hole 232, 234 below the end cap 228. This cover cap is preferably threadingly engaged with a second internally threaded surface 240 of the outer pylon 212, the second internally threaded surface 240 having a larger diameter than that of the first internally threaded surface 230. Along the surface that secures end cap 228, the cover cap 238 is provided with an O-ring notch 242 that abuts against the horizontal surface 244 between the surfaces 230 and 240. By providing an O-ring 246 into this notch, when the cover cap is screwed into the internally threaded surface 240 against the horizontal surface 244, the O-ring 246 is compressed to provide a seal with respect to the interior of pylon 212.

The cover cap 238 preferably includes a valve 248 to control the passage of fluid from inside the inner pylon to a reservoir 250 contained within the outer pylon. This reservoir is defined on its sides by the internally threaded surface 240, at one end by the cover cap 238, and at its other end by a reservoir cap 252 which is also threadingly engaged in the surface 240. Below the threaded surface 240 the bottom of the outer pylon 212 on its inside surface 254 is preferably non-threaded, and the reservoir cap 252 has a larger diameter portion at its bottom that abuts against the horizontal surface 256 between surfaces 240 and 254. An O-ring notch 258 is provided in the reservoir cap, and O-ring 260 is inserted into the notch which compresses against horizontal surface 256 to form a fluid tight seal.

The torque-resisting cuff 226 is preferably configured to oscillate between a relatively straight vertical position, when the outer pylon and inner pylon are moved relatively far apart, and a curved position, when the outer pylon and inner pylon are compressed relative to one another. FIG. 23 illustrates the shock module 210 in a fully compressed configuration such that the cuff 226 is curved and the inner pylon 214 extends as far as possible into the outer pylon 212. More particularly, when fully compressed the enlarged outer diameter portion of the inner pylon 214 preferably abuts against the proximal end of the outer pylon 212.

Similar to the syringe system described with respect to FIGS. 15A-16A above, the telescoping pylons of the active shock module 210 generate pressure within the bladder 206 by the amputee's motion causing the pylons to move toward and away from each other. More particularly, the relative motion of the pylons, in conjunction with the compressible fluid and/or spring or other compressible medium inside the pylons, causes fluid pressure to build up within the inner pylon. Pressure may also be regulated within the inner pylon through the valve 224. Valve 248 at the bottom of the inner pylon regulates fluid pressure and can be opened to transfer fluid into the reservoir 250. Fluid line 236 preferably connects the reservoir to the bladder 206, and valve 264 controls the flow of fluid into the bladder in order to adjust the pressure inside the bladder. It will further be appreciated that pressure step-up or amplification may be provided by changing the relative sizing of the telescoping pylons.

It will be appreciated that although the active shock module has been described with respect to inflatable bladder 206, the shock module may also be used with other inflatable members, such as the stiffener of FIG. 11D. Furthermore, an active shock module may be used to inflate multiple members, such as shown in FIGS. 10, 13, and 14.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A prosthetic foot, comprising:
an elongate upper element;
an elongate lower element;
a resilient member positioned between the upper element and the lower element; and
an insertion element positioned in the resilient member, wherein the insertion element is rotatable between the upper and lower elements from a first position to a second position, wherein in the first position and the second position the insertion element is completely between the upper and lower elements, and wherein rotation of the insertion element causes stiffness to vary in a particular location of the resilient member.

2. The prosthetic foot of claim 1, wherein the upper element and lower element are formed of the same material.

3. The prosthetic foot of claim 1, wherein the upper element and lower element are formed of fiberglass.

4. The prosthetic foot of claim 1, wherein there is angular rotation of the upper element relative to the lower element.

5. The prosthetic foot of claim 1, wherein rotation of the insertion element changes the orientation of the insertion element.

6. The prosthetic foot of claim 1, wherein at least two insertion elements are positioned in the resilient member.

7. The prosthetic foot of claim 6, wherein the two insertion elements are capable of rotation simultaneously.

8. The prosthetic foot of claim 1, wherein the insertion element has a stiffness greater than the stiffness of the resilient member.

9. The prosthetic foot of claim 1, further comprising a strap attached to the upper element and the lower element.

10. The prosthetic foot of claim 1, wherein the lower element comprises a curvilinear plate.

11. The prosthetic foot of claim 10, wherein the upper element comprises a curvilinear plate.

12. The prosthetic foot of claim 10, wherein the lower element is formed of a plurality of lamina.

13. The prosthetic foot of claim 10, wherein the lower element is formed a fiber composite.

14. A prosthetic foot, comprising:
an ankle plate;
a foot plate having a front end and a back end;
a resilient ankle member positioned between the foot plate and the ankle plate, the resilient ankle member including one or more slots; and
one or more insertion elements positioned in the one or more slots, wherein the insertion elements comprise cylindrical rods attached to arms joined in a middle chamber by an actuator, wherein movement of the one or more insertion elements from a first position to a second position relative to the ankle plate and foot plate causes stiffness to vary in a particular location between the ankle plate and the foot plate, the one or more insertion elements positioned in the slot in both the first and second positions.

15. The prosthetic foot of claim 14, wherein the insertion elements are capable of translational movement.

16. A prosthetic foot, comprising:
an ankle plate;
a foot plate having a front end and a back end;
a resilient ankle member positioned between the foot plate and the ankle plate, the resilient ankle member including one or more slots; and
one or more insertion elements positioned in the one or more slots, wherein the insertion elements are rotatable, wherein movement of the one or more insertion elements from a first position to a second position relative to the ankle plate and foot plate causes stiffness to vary in a particular location between the ankle plate and the foot plate, the one or more insertion elements positioned in the slot in both the first and second positions.

17. The prosthetic foot of claim 16, wherein the resilient ankle member is formed of urethane or rubber.

18. The prosthetic foot of claim 16, wherein the insertion elements comprise cylindrical rods.

19. A prosthetic foot, comprising:
an elongate upper element;
an elongate lower element;
a resilient member positioned between the upper element and the lower element; and
an insertion element positioned in the resilient member, wherein the insertion element comprises a rotatable cam, wherein movement of the insertion element between the upper and lower elements causes stiffness to vary in a particular location of the resilient member.

20. The prosthetic foot of claim 19, wherein the rotatable cam is formed of a material having stiffness greater than the stiffness of the block.

* * * * *

UNITED STATES PATENT AND TRADEMARK OFFICE
CERTIFICATE OF CORRECTION

PATENT NO.        : 7,879,110 B2                              Page 1 of 1
APPLICATION NO.   : 12/628996
DATED             : February 1, 2011
INVENTOR(S)       : Van L. Phillips It is certified that error appears in the above-identified patent and that said Letters Patent is hereby corrected as shown below:

Title Page;

On page 1, delete "(73) Assignee: Ossur hf (IS)".

Signed and Sealed this
Twenty-seventh Day of September, 2011

David J. Kappos
*Director of the United States Patent and Trademark Office*